(12) United States Patent
Le Fur

(10) Patent No.: US 10,241,169 B2
(45) Date of Patent: Mar. 26, 2019

(54) METHOD FOR ANALYSIS BY NUCLEAR MAGNETIC RESONANCE OF A SAMPLE INCLUDING A SPECIES TO BE CHARACTERIZED AND A REFERENCE SPECIES

(71) Applicants: UNIVERSITÉ D' AIX-MARSEILLE, Marseilles (FR); CENTRE NATIONAL DE LA RECHERCHE SCIENTIFIQUE, Paris (FR)

(72) Inventor: Yann Le Fur, Marseille (FR)

(73) Assignees: CENTRE NATIONAL DE LA RECHERCHE SCIENTIFQUE, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 931 days.

(21) Appl. No.: 14/655,765

(22) PCT Filed: Dec. 24, 2013

(86) PCT No.: PCT/EP2013/078007
§ 371 (c)(1),
(2) Date: Jun. 26, 2015

(87) PCT Pub. No.: WO2014/102293
PCT Pub. Date: Jul. 3, 2014

(65) Prior Publication Data
US 2015/0362571 A1    Dec. 17, 2015

(30) Foreign Application Priority Data
Dec. 28, 2012  (FR) .................................... 12 62964

(51) Int. Cl.
*G01R 33/46* (2006.01)
*G01N 24/08* (2006.01)
(Continued)

(52) U.S. Cl.
CPC ......... *G01R 33/4625* (2013.01); *G01N 24/08* (2013.01); *G01R 33/465* (2013.01); *G01R 33/3415* (2013.01)

(58) Field of Classification Search
CPC ... G01R 33/4625; G01R 33/465; G01N 24/08
See application file for complete search history.

(56) References Cited

U.S. PATENT DOCUMENTS

| 4,354,499 A | 10/1982 | Damadian |
| 4,651,098 A * | 3/1987 | Yamada ................. G01R 33/54 324/309 |

(Continued)

FOREIGN PATENT DOCUMENTS

| CA | 2674250 | 10/2010 |
| JP | 60102544 A | 6/1985 |

OTHER PUBLICATIONS

Maril et al., "An automated algorithm for combining multivoxel MRS data acquired with phased-array coils," Journal of Magnetic Resonance Imaging 21, 317-322, (2005).

(Continued)

*Primary Examiner* — Dixomara Vargas
(74) *Attorney, Agent, or Firm* — Young & Thompson

(57) ABSTRACT

Method for analyzing, using nuclear magnetic resonance, at least one sample including at least one species to be characterized and a reference species having a content, in the sample, that is more than twice greater than the content of the species to be characterized, the method includes:
applying at least one constant field $B_0$ to the at least one sample;
acquiring, using one or more antenna(s), one or more complex free induction decay (FID) signal(s) $S(t)$, with each complex FID signal $S(t)$ including a real part and an imaginary part; with the acquisition step being carried out such that, in each complex FID signal $S(t)$, (Continued)

the amplitude of the signal of the reference species is at least twice greater than the amplitude of the signal of the at least one species to be characterized; and for each complex FID signal S(t), calculating the module of each complex FID signal S(t).

35 Claims, 24 Drawing Sheets

(51) Int. Cl.
  *G01R 33/465* (2006.01)
  *G01R 33/3415* (2006.01)

(56) References Cited

U.S. PATENT DOCUMENTS

| | | | | |
|---|---|---|---|---|
| 5,289,127 | A * | 2/1994 | Doddrell | G01R 33/56518 324/309 |
| 5,678,548 | A * | 10/1997 | Murugesan | G01R 33/60 600/413 |
| 6,208,137 | B1 * | 3/2001 | Sardashti | G01R 33/4625 324/300 |
| 6,549,007 | B1 * | 4/2003 | Hills | G01R 33/307 324/303 |
| 6,696,838 | B2 * | 2/2004 | Raftery | G01R 33/307 324/310 |
| 6,958,609 | B2 * | 10/2005 | Raftery | G01R 33/307 324/307 |
| 7,064,544 | B1 | 6/2006 | Schirmer | |
| 2002/0130661 | A1 * | 9/2002 | Raftery | G01R 33/307 324/318 |
| 2004/0095139 | A1 | 5/2004 | Brown | |
| 2004/0164738 | A1 * | 8/2004 | Raftery | G01R 33/307 324/321 |
| 2008/0204022 | A1 | 8/2008 | Sillerud et al. | |
| 2011/0288802 | A1 * | 11/2011 | Takegoshi | G01N 24/08 702/76 |
| 2017/0052238 | A1 * | 2/2017 | Le Fur | G01R 33/4625 |

OTHER PUBLICATIONS

Brown, M. A., "Time-domain combination of MR spectroscopy data acquired using phased-array coils," Magnetic Resonance in Medicine 52, 1207-1213 (2004).
Natt et al, Use of phased array coils for a determination of absolute metabolite concentrations. Magnetic Resonance in Medicine 53, 3-8, (2005).
Martini et al., "Noise correlations and SNR in phased-array MRS," NMR in Biomedicine 23, 66-73, DOI:10.1002/nbm.1429 (2010).
Brown et al., "NMR spectral quantitation by principal-component analysis. II. Determination of frequency and phase shifts," Journal of Magnetic Resonance, Series B 112,32-43 (1996).
Le Fur et al., "Grid-free interactive and automated data processing for MR chemical shift imaging data," Magn. Reson. Mater. Phy. 23, 23-30 (2010).
Maudsley et al., "Comprehensive processing, display and analysis for in vivo MR spectroscopic imaging," NMR in Biomedicine, 19, 492-503 (2006).
Soher et al., "Quantitative proton MR spectroscopic imaging of the human brain," Magnetic Resonance in Medicine 35, 356-363 (1996).
Ebel et al., "Detection and correction of frequency instabilities for volumetric 1H echo-planar spectroscopic imaging," Magnetic Resonance in Medicine 53, 465-469 (2005).
Stefan et al., "Quantitation of magnetic resonance spectroscopy signals: the jMRUI software package," Measurement Science and Technology 20 (2009), pp. 1-9.
Bydder et al., "Optimal phased-array combination for spectroscopy," Magnetic Resonance Imaging, 26 (2008), pp. 847-850.
Dong et al., "The rapid and automatic combination of proton MRSI data using multi-channel coil without water suppression," Magnetic Resonance Imaging, 25 (2007), pp. 1148-1154.
Klose, "In Vivo Proton Spectroscopy in Presence of Eddy Currents," Magnetic Resonance in Medicine 14, pp. 26-30 (1990).
Prock et al., "An algorithm for the optimum combination of data from arbitrary magnetic resonance phased array probes," Physics in Medicine and Biology 47 (2002), pp. N39-N46.
Rodgers et al., "Receive Array Magnetics Resonance Spectroscopy: Whitened Singular Value Decomposition (WSVD) Gives Optimal Bayesian Solution," Magnetic Resonance in Medicine 63, pp. 881-891 (2010).
Sandgren et al., "Spectral analysis of multichannel MRS data," Journal of Magnetic Resonance 175 (2005), pp. 79-91.
Schaffter et al., "Fast 1H Spectroscopic Imaging Using a Multi-Element Head-Coil Array," Magnetic Resonance in Medicine 40, pp. 185-193 (1998).
Serrai et al., "Localized Proton Spectroscopy without Water Suppression: Removal of Gradient Induced Frequency Modulations by Modulus Signal Selection," Journal of Magnetic Resonance 154 (2002), pp. 53-59.
Gilbert, "Chapitre 4: Article 1: Impact of an improved combination of signals from array coils in diffusion tensor imaging," Thesis of Guillaume Gilbert, section 4.5.2.
Reutter et al., "Compensation of Magnetic Field Instabilities in Field Cycling NMR by Reference Deconvolution," Applied Magnetic Resonance (2013) 44:55-63.
Jiru, "Introduction to post-processing techniques," European Journal of Radiology, vol. 67. No. 2. Aug. 1, 2008, pp. 202-217.
Poullet et al, "MRS signal quantitation: A review of time- and frequency-domain methods," Journal of Magnetic Resonance, vol. 195 (2008), pp. 134-144.
Ozdemir et al., "Quantitative proton magnetic resonance spectroscopy without water suppression," Journal of Instrumentation, vol. 4, No. 6, Sep. 22, 2007.
Sousa et al., "Desktop fast-field cycling nuclear magnetic resonance relaxometer," Solid State Nuclear Magnetic Resonance, vol. 38, Jul. 16, 2010, pp. 36-43.
Gonen et al., "Solvent Suppression by Selective Signal Subtraction, a Time-Domain Negative-Feedback Dynamic-Range-Compression Method for Proton NMR Spectroscopy," Journal of Magnetic Resonance Series B, vol. 102, Aug. 1993, pp. 98-102.
Skoch et al., "Spectroscopic imaging: Basic principles," European Journal of Radiology, vol. 67, Aug. 1, 2008, pp. 230-239.
Lattanzi, "G16.4426/EL5823/BE6203 Medical Imaging: MRI Instrumentation, Data Acquisition, Image Reconstruction," Apr. 23, 2012.
Oct. 12, 2017, JP communication issued for related JP application No. 2015550076.

* cited by examiner

METHOD FOR ANALYSIS BY NUCLEAR MAGNETIC RESONANCE OF A SAMPLE INCLUDING A SPECIES TO BE CHARACTERIZED AND A REFERENCE SPECIES

TECHNICAL FIELD OF THE INVENTION

The present invention generally relates to nuclear magnetic resonance (NMR) techniques used in particular for analyzing samples. The present invention advantageously applies to the field of medicine for analyzing biological samples from human bodies for example or to the field of chemistry for analyzing chemical compositions. It is particularly advantageous for correcting the phase and/or the frequency of a free induction decay (FID) signal. In one advantageous but non-limiting application, the invention will be used for effectively recombining the NMR signals detected by antenna arrays.

STATE OF THE ART

Nuclear magnetic resonance (NMR) was discovered in the forties, and has become increasingly important in many areas of science for analyzing materials and more particularly in medicine for the in vivo observation of the human body. Numerous applications of this discovery have been implemented. In the medical field, magnetic resonance imaging or MRI and NMR spectroscopy makes it possible to analyze the composition of body tissues. Within the scope of the present invention, the terms spectroscopy and spectrometry will be interchangeably used as such techniques make it possible to identify and/or quantify the content of species in a sample.

Nuclear magnetic resonance is a complex phenomenon which is completely described by the laws of quantum physics only. For understanding the invention and the prior art it is however sufficient to know the main phenomena implemented by NMR and briefly summarized below. It should be noted here that a very abundant technical literature dealing with all aspects of the NMR already exists.

When placed in a strong magnetic field, conventionally designated $B0$, typically of the order of one tesla (T) or more, some atoms acquire specific properties such that, if disturbed by a radio wave having an appropriate frequency, they return a signal that can be analyzed.

The atoms involved are those with an atomic nucleus with a non-zero magnetic moment or spin. In the medical field, hydrogen (H) of the water (H2O), which constitutes the major part of the human body has this property. The water molecule has two hydrogen nuclei or protons having a non-zero spin driven by a precession movement of their axis at a particular frequency called the Larmor frequency. When placed in a strong external static magnetic field, the nuclei then have their spins orientated either in the direction of the external magnetic field, or in the opposite direction while undergoing a precession movement at the Larmor frequency depending on the intensity of the external field $B0$. As regards hydrogen nuclei, the Larmor frequency increases by 42 MHz (1 megahertz=$10^6$ hertz) per tesla. It is for example close to 4 MHz for 0.1 T; 64 MHz for 1.5 T and 600 MHz for 14 T.

The nuclei may then be disturbed by a radio wave or radio frequency (RF) all the more easily since the frequency thereof is close to the Larmor frequency and therefore preferably resonating therewith. The disturbance has the effect of changing the orientation of the spin until it is possibly switched to the other direction allowed by the external magnetic field $B0$. This means that the orientation is parallel or antiparallel thereto and switches from one to the other. Conventionally designated $B1$, the magnetic induction of the disturbing radio wave is applied perpendicularly to that of $B0$ to switch the spin of the nuclei. Such switching and the return to a steady-state or relaxation generate the electrical signal detected in all NMR equipment. This signal is commonly referred to as FID for "free induction decay".

The electromagnetic disturbance $B1$ is applied using electrical coils usually called antennas. The coils or antennas are generally used both for applying the disturbance and for detecting the electrical signals generated during the return to a steady-state of the nuclei. For this purpose, they are associated on the one hand with electronic circuits which will enable an electric current to circulate for a controlled time at the Larmor frequency, which will generate, in the region of the analyte, the electromagnetic wave and the disturbing field $B1$, and on the other hand with electronic circuits which will make it possible to detect the electrical signals generated by the return to a steady-state of the nuclei after the electromagnetic disturbance has been interrupted. It should be noted here that the electrical signals which must be detected with these antennas are usually low or very low, and that the challenge is to distinguish these from the level of the intrinsic noise of the electrical equipment used. The signal to noise ratio (SNR) is the key criterion for the electrical detection part of any NMR equipment. It must be high enough to enable the detection of the signals at a level above the noise which makes these usable by the considered application.

As will be described in greater details below while referring to FIG. 1, the known techniques consist in performing a Fourier transform of the FID complex signal to obtain a spectral distribution of the sample. Such spectral distribution makes it possible to compare the frequency and the amplitude of a reference signal with those of the signals of the metabolites to be characterized.

The reference signal usually corresponds to a major species in the sample. For analyzing a biological sample, the reference signal is typically the water signal.

Comparing the frequency and the amplitude of the water signal with those of the signals of the metabolites to be characterized makes it possible to identify the nature and the content of the metabolites in the sample.

This technique is globally satisfactory. It nevertheless requires the acquired reference signal to be correctly positioned, as regards the phase and the frequency with respect to a theoretical position. The reference signal is then said to be "resonating". For this purpose, the conversion frequency of the receiver, typically a coil, must be set, exactly on the resonance frequency of the reference signal.

Now, many parameters tend to show a frequency shift which separates the acquired reference signal from its theoretical position.

As will be detailed later, such shift at least partially results from the difference existing, in practice, between the demodulation frequency used by the receiver and the actual frequency of the reference signal.

The known techniques thus require to manually correct the phase and the frequency of the complex FID signal prior to using it. Such correction steps are relatively long and tedious.

Besides, another manual correction operation consists in re-phasing the reference signal. As a matter of fact, in practice, a random offset necessarily exists between the phase of the signal used by the receiver and the phase of the reference signal. This is shown, in a representation of a complex FID signal, by the fact that the first point of the FID is generally not real.

In addition, in the cases where signals from several volumetric entities of the sample, usually designated voxels, are acquired, the inhomogeneity of the field $B_0$ also tends to result in phase shifts and frequency offsets.

Furthermore, phase shifts and frequency offsets are also generated by the use of multiple antennas. As a matter of fact, during the decades of development, the antenna structures have known a significant evolution and the research and development of NMR equipment now tend to promote the use of multiple antennas for analyzing a given area of the human body. Such multiple antennas are generally identical and have a small size and the signals detected separately are combined in order to obtain a composite signal with a significantly better SNR than if it had been obtained with a single antenna covering the same area of analysis. Furthermore, using a plurality of antennas will generally increase the speed of acquisition, while maintaining a good SNR, which proves essential when the sample belongs to a living body and is therefore often not perfectly still. This type of antenna, called "phased array antenna", is characterized by a significantly increased complexity of electronics and computer processing of the signals produced separately by each of the antennas in the array. As a matter of fact, it must be possible to recombine them effectively, despite the inevitable geometric, physical and electrical differences between the antennas which must be compensated for actually obtaining the expected improvements of the antenna array. The document US 2004/0095139 discloses a solution for recombining the FID signals delivered by several coils.

Therefore an object of the present invention consists in providing a method for simplifying and improving the correction of phase and/or frequency of the NMR signals detected by the antennas, such as coils.

Furthermore, it would be particularly advantageous to improve the SNR of the signals obtained, with respect to the known methods.

It would also be particularly advantageous to provide a solution for improving the recombination of the NMR signals detected separately by one or more antenna(s) without significantly complicating the known equipment.

Another advantage consists in providing a solution for simplifying the complexity of NMR equipment, specifically those using several receiver coils.

Other objects, characteristics and advantages of the invention will appear upon reading the following description and the appended drawings. It should be understood that other advantages can be integrated.

SUMMARY OF THE INVENTION

According to one embodiment, the invention relates to a method for the spectroscopic analysis, using nuclear magnetic resonance (NMR), of at least one sample comprising at least one species to be characterized and a reference species, the content in the sample which is more than twice greater than the content of the at least one species to be characterized, with the method comprising the following step:

a. applying one constant field $B_0$ to the at least one sample, b. acquiring by one or more antenna(s) one or more complex free induction decay (FID) signals S(t), with each FID complex signal S(t) comprising a real part and an imaginary part; with the step of acquiring being performed so that, in each complex FID signal S(t) the amplitude of the signal of the reference species is at least twice greater than the amplitude of that of the least one species to be characterized;

characterized in that the method also comprises at least the steps of:

c. for each complex FID signal S(t), extracting the module of each complex FID signal.

According to a preferred embodiment, the method comprises a subsequent step of applying a Fourier transform to a signal taking into account the FID module. This step is optional. It makes it possible to generate a spectral representation of the sample. According to another embodiment, the signal is stored in the time domain. Such other embodiment will be chosen for example to generate a metabolic map by CSI.

The complex free induction decay (FID) signals each comprise data relating to the reference species. Thus, before generating the FID module, the method according to the invention retains the signal of the reference species. Preferably, the invention therefore provides no complete removing of the reference species before extracting the FID module. A partial suppression is possible, but the amplitude of the reference species signal must however be at least greater than twice the amplitude of the signal of the species to be characterized before extracting the FID module.

The signal of the reference species is then used as a carrier for the signals of the species to be characterized. The phase information of the signals of the species to be characterized is thus preserved despite the taking into account of the module.

Thus, with the invention, as soon as the signal of the reference species is acquired, typically water signal, the real and imaginary parts can be omitted. Then, the signal of the reference species can be suppressed or greatly reduced after correcting the phase of the signal by taking the module into account.

By applying the method according to the invention, a symmetrical spectrum is obtained on either side of the frequency corresponding to that of the major species, typically water when the sample is a biological tissue.

Although some of the information captured by the antennas (phase information) is suppressed when taking into account the FID module, the final signal to noise ratio of the signal (SNR) remains perfectly satisfactory. Within the scope of the development of the present invention, it was expected that this loss of information would lead to too detrimental a drop of the SNR. Obtaining a very satisfying SNR probably comes from the fact that the loss of information is largely compensated by the automatic elimination of the phase shifts and the frequency offsets allowed by the sequence of steps according to the invention, while taking into account the module in a signal having a carrier and weaker signals representative of the species to be characterized. As a matter of fact, the invention makes it possible to automatically correct the phase shifts and frequency offsets resulting, in particular, from sample movements during the FID, the inhomogeneities of the field $B_0$ and the inevitable changes in the behaviour of the various antennas within the scope of an acquisition by several antennas.

The spectrum obtained is thus used to identify and to very easily characterize the species in the sample.

In a particularly advantageous manner, the invention also eliminates the need for additional steps specifically dedicated to correcting the phase and the frequency, with such steps usually requiring significant processing time, often even a manual action by an operator.

In addition, the amount of data to be processed is half that which must be conventionally processed where the complex signal is required for calculating the phase shift of the signal. In addition, the module can be calculated in the real domain since it suffices to take the square root of the sum of two numbers, each one being squared, while the phase calculation requires working with complex numbers, which is more difficult to implement. The time and cost of processing are significantly reduced, and the fact that the manual action by an operator is no longer required allows for the automatic processing in real time without affecting the users.

The invention thus offers significant advantages as regards accuracy, reliability, reproducibility, processing times and cost reduction.

Optionally but advantageously, the method according to the invention may also comprise at least one of the following optional steps and characteristics which may be taken alone or in combination:

According to one embodiment, the method comprises, after the extraction of the module of each complex FID signal S(t), a step of identifying the nature and the content of the at least one species to be characterized from the module of each complex FID signal S(t).

According to one embodiment, the method comprises, after the extraction of the module of each complex FID signal S(t) and prior to the identification of the nature and the content of the at least one species from the characterizing module of each complex FID signal, a step of applying a Fourier transform to a signal taking into account said FID module.

According to one embodiment, the content of the reference species in the solvent is at least greater than 5 times, preferably 10 times, preferably $10^3$ times and more preferably $10^5$ times the content of each species to be characterized. In the present invention, the content of the at least one species to be characterized is the mass content in the sample. According to one embodiment, the signal of the reference species is used as a carrier for the signal of the at least one species to be characterized. According to one embodiment, the content of the reference species in the sample is sufficiently higher than the content of the species to be characterized in the sample for the signal of the reference species to be used as the carrier for the signal of the at least one species to be characterized. The reference species has a resonance frequency.

According to one embodiment, the relative content of the reference species and of the at least one species to be characterized, as well as their relative relaxation time are so chosen that the amplitude of the signal of the reference species is at least twice the amplitude of one of the at least one species to be characterized. The sample is thus so selected that, in each acquired complex FID signal S(t), the amplitude of the reference signal of the species is at least twice the amplitude of that of the at least one species to be characterized. Preferably, the sample is so selected that in each acquired FID complex signal S(t), the amplitude of the signal of the reference species is at least three times, or even at least five times, or even at least ten times greater than the amplitude of that of each of the species to be characterized.

The FID module of a sample comprising the species to be characterized is equal to ||S(t)|| which is defined by the following equation:

$$\|S(t)\| = |A_{H2O}(t) + A_0(t)\cos(\Delta\omega t + \Delta\varphi)|$$

where:

$\Delta\omega = \omega - \omega_{H2O}$ and $\Delta\varphi = \varphi - \varphi_{H2O}$ respectively correspond to the frequency offsets and phase shifts between the at least one species to be characterized and the reference species, $A_{H2O}(t)$ is the amplitude versus time of the FID signal from the reference species, $A_0(t)$ is the amplitude versus time of the FID signal of the species to be characterized.

According to one embodiment, during the step of acquiring complex FID signals S(t) delivered by several voxels of the sample are acquired, and a step of spatial filtering is performed after calculating the module of the complex FID signal S(t) for each of the voxels.

Such sequence of steps (calculation of the module and spatial filtering) makes it possible to significantly improve the SNR. The invention thus provides a significant advantage within the scope of the CSI.

According to an advantageous embodiment, during the step of acquiring a plurality of complex free induction decay (FID) signals are acquired.

Advantageously, after the step of generating a FID module for each complex free induction decay (FID) signal of the plurality of complex free induction decay (FID) signals, a summation of the FID modules is performed for obtaining a combined FID signal.

Advantageously, said Fourier transform is applied to the combined FID signal. The step of acquiring is preferably so performed that, in each spectral representation of the complex FID signal, the amplitude of the signal of the reference species is preferably at least twice the amplitude of that of the at least one species to be characterized.

According to one advantageous embodiment, the antennas are coils and the acquired complex FID signals are delivered by the same coil. In this embodiment, the invention advantageously makes it possible to make an effective and simple correction of the phase shift and frequency offset due in particular to the sample movements during the acquisition.

According to an advantageous embodiment, the antennas are coils and the acquired complex FID signals are delivered by different coils. In this embodiment, the invention advantageously makes it possible to execute an effective and simple correction of the phase shift of each coil with respect to each other, and to the phase shift and frequency offset due in particular to the inhomogeneity of the field B0.

According to one advantageous embodiment, the antennas are coils and the acquired complex FID signals are delivered by different coils and several complex FID signals are acquired for at least some coils. In this embodiment, the invention advantageously enables an efficient and simple correction of the phase shift and the frequency offset more particularly caused by the movements of the sample and the inhomogeneity of B0.

Advantageously, after the generation of a FID module for each complex FID signal, and prior to the summing of the FID modules to obtain a combined FID signal, a step of calculating a weighting factor for each coil is executed and each FID module is weighted by the weighting factor of the coil by which it has been delivered. The step of calculating a weighting factor is advantageously performed using the method of the sum of squares of the amplitudes at the start of the FID module.

According to one embodiment, during the step of acquiring, a single complex free decay induction (FID) signal S(t) is acquired, and a Fourier transform is applied to a FID module obtained by extracting the module from such single complex FID signal.

According to one embodiment, during the step of acquiring, a spatially encoded FID signal is acquired, this acquisition is repeated several times, preferably at least twice, to obtain several encoded signals, with each of said encoded signals being subsequently decoded so that it is associated with a voxel of the sample and a FID module is generated for the FID signal associated with each voxel.

Preferably, during the step of acquiring, several complex free induction decay (FID) signals are acquired. Such complex FID signals comprise a spatial encoding depending on the position of a plurality of voxels of the sample, and these complex signals are decoded to obtain a FID signal associated with each voxel and a FID module is generated for the FID signal associated with each voxel.

According to one embodiment, the sample is a sample of biological material, the reference species is water and the species to be characterized are metabolites. According to an alternative embodiment, the sample is a chemical composition, the reference species is water or another solvent and the species to be characterized are chemical compounds.

According to one embodiment, the sample comprises several species to be characterized.

According to one embodiment, the constant field B0 is applied to several voxels of a sample and the frequency spectra of the combined FID signals of the different voxels are used to generate one or more spectroscopic image(s).

Prior to the acquisition of the FID signals, a conventional step of settings necessary for performing an NMR spectroscopy experiment is carried out.

According to a particular embodiment, the following steps are performed after the step of acquiring one or more complex FID signals S(t) by one or more antenna(s) prior to calculating the module:
  obtaining a FID spectrum $S(\omega)$ by applying a Fourier transform to the real and complex parts of the at least one complex FID signal S(t), with the FID spectrum $S(\omega)$ obtained then comprising the reference species and the species to be characterized and having two portions (UFR, DFR) each extending from the resonance frequency of the reference species ($F_{0Ref}$) respectively on either side of $F_{0Ref}$, with the frequency of the species to be characterized being located on a first portion of the spectrum taken among said two portions (UFR, DFR);
  modeling the signal of the reference species Sref(t) from the real and complex parts of the at least one complex FID signal S(t);
  obtaining a spectrum Sref($\omega$) of the reference species by applying a Fourier transform to the modeling of the signal of the reference species Sref(t), with the spectrum Sref($\omega$) of the reference species then having two spectrum portions extending from the resonance frequency of the reference species ($F_{0Ref}$) of the spectrum Sref($\omega$) and extending respectively on either side of $F_{0Ref}$;
  obtaining (1324) a modified FID spectrum $\tilde{S}(\omega)$, by substituting a second portion of the FID spectrum S($\omega$), with said second portion being the portion taken from said two portions (UFR and DFR) of the spectrum S($\omega$) and which does not comprise the species to be characterized, by the portion of the spectrum Sref($\omega$) taken from the two portions of the spectrum extending from $F_{0Ref}$ of the spectrum Sref($\omega$) and extending on the same side as said second portion of the spectrum S($\omega$);
  applying an inverse Fourier transform to the modified spectrum $\tilde{S}(\omega)$ to obtain a modified FID signal $\tilde{s}(t)$ in the time domain;
  calculating the module of the modified FID signal $\tilde{s}(t)$;
  identification and/or quantification of the species to be characterized from the module of the modified FID signal $\tilde{s}(t)$.

A step of identifying and/or quantifying the species to be characterized can then be performed from the module of the modified FID signal $\tilde{s}(t)$.

The invention makes it possible to obtain an improved SNR. As a matter of fact, taking into account the module makes it possible to automatically correct the phase and frequency shifts due in particular to the sample movements during the FID, to the field B0 inhomogeneities and to the inevitable changes in the behaviour of the various antennas within the scope of an acquisition by several antennas. The signal of the reference species is used as the carrier for the signals of the species to be characterized and the phase information of the latter is preserved in spite of the taking into account of the module.

Thus, the spectrum obtained makes it possible to identify and to very easily characterize the sample species.

Moreover, replacing a portion of the spectrum S($\omega$) by a portion of the spectrum Sref($\omega$) resulting from the modeling of the reference species, makes it possible to obtain the modified spectrum $\tilde{S}(\omega)$ which has no noise on the portion thereof which does not comprise the species to be characterized. The signal $\tilde{s}(t)$ from which the module is calculated then has only the noise from the spectrum portion S($\omega$) comprising the species to be characterized. The above steps preceding the calculation of the module of the modified FID signal $\tilde{s}(t)$ thus make it possible to avoid a superimposition of the noises originally carried by the two portions of the spectrum S($\omega$) during the taking into account of the module. The SNR of the signal obtained is thus significantly improved, since the disadvantages inherent in the taking into account of the module are limited or even eliminated by these steps.

Besides, as compared to known solutions, the module of the invention makes it possible not to resort to additional steps specifically dedicated to the phase and frequency corrections, with such steps usually requiring significant processing time, often even a manual action by an operator.

This method is particularly advantageous within the scope of a spectroscopic/spectrometric nuclear magnetic resonance (NMR) analysis of a sample. It makes it possible to easily identify and/or quantify the sample species.

According to an advantageous embodiment, the method comprises: a step of calculating 1314 the module of the FID signal S(t) and the following steps executed after calculating the module of the modified FID signal $\tilde{s}(t)$ and prior to the step of identifying and/or quantifying the species to be characterized:
  either: subtracting the module of the signal S(t) from the modified FID signal module $\tilde{s}(t)$ and then subtracting the result obtained in the previous step from the module of the modified FID signal $\tilde{s}(t)$;
  or: applying a Fourier transform to the module of the signal S(t) and the module of the modified FID signal $\tilde{s}(t)$; subtracting the spectrum of the module of the signal S(t) from the spectrum of the module of the modified FID signal $\tilde{s}(t)$; then subtracting the result obtained in the previous step from the spectrum of the module of the modified FID signal $\tilde{s}(t)$.

Thus, the first subtraction is equivalent to isolating the "sidebands" which are present in the modified signal $\tilde{s}(t)$ after the step of "calculating the module of the modified FID signal $\tilde{s}(t)$" whereas they had been previously removed by the taking into account of the module of the signal S(t). As for the second subtracting, it makes it possible to eliminate the sidebands of the modified FID signal $\tilde{s}(t)$. The invention thus makes it possible to efficiently eliminate the sidebands and more generally all the antisymmetric artefacts, i.e. the artefacts having frequencies distributed symmetrically with respect to the resonance frequency of the reference signal, the amplitudes of which are equal and have opposite signs.

According to one embodiment, during the step of acquiring, complex FID signals S(t) from several voxels of the sample are acquired, and a spatial filtering step is performed after calculating the module of the modified FID signal $\tilde{s}(t)$ for each of the voxels.

The spatial filtering is applicable since CSI are concerned, whether they are acquired by one or more coil(s).

Typically, the spatial filtering comprises the following steps in the case of a CSI having two spatial dimensions: multiplying each row and each column of the CSI matrix, using a "bell" (e.g. Gaussian, cosine, Hanning, Hamming, ...) function prior to a Fourier transform in the spatial domain. This is the reason why, when a spatial filtering is desired to be executed after calculating the module, the inverse Fourier transform is executed in the spatial domain so as to return to the k space.

This represents an important advantage within the scope of a particular CSI. As a matter of fact, if the spatial filtering is performed after processing the module, the spectra of the voxels of the CSI are aligned in phase and frequency. On the contrary, if the spatial filtering is executed prior to extracting the module, the voxels concerned are not aligned in phase and frequency and the resolution of the resulting spectrum can be degraded, thus causing a decrease in the SNR. It should be reminded here that a CSI analysis involves the processing of a plurality of voxels and may for example result in a plurality of spectra, with each corresponding to a voxel or a two-dimension image, for example.

According to one advantageous embodiment, during the step of acquiring, a single complex FID signal S(t) is acquired, a unique FID spectrum S(ω) is obtained by applying a Fourier transform to the real and complex parties of said single complex FID signal S(t). During the step of identifying and/or quantifying the species to be characterized, a Fourier transform is applied to a single module of the modified FID signal $\tilde{s}(t)$.

According to one embodiment, after the step of calculating the module of the modified FID signal $\tilde{s}(t)$ and for identifying and/or quantifying the species to be characterized from the module of the modified FID signal $\tilde{s}(t)$, a Fourier transform can, according to one embodiment, be applied to a signal comprising at least the module of the modified FID signal $\tilde{s}(t)$. The FFT is preferably applied to the module of the modified FID signal $\tilde{s}(t)$. A spectrum is thus obtained, whereon it is very easy, even for an operator to identify the species by their frequency and to quantify same by the peak area they define. If the sample comprises several voxels, one spectrum per voxel will then be obtained.

After the step of calculating the module of the modified FID signal $\tilde{s}(t)$ and for identifying and/or quantifying the species to be characterized from the module of the modified FID signal $\tilde{s}(t)$, applying a Fourier transform to a signal comprising at least the module of the modified FID signal $\tilde{s}(t)$ can, according to another embodiment, be avoided. The identification and/or quantification is then carried out in the time domain. In this case, well-known software makes it possible to sum elementary FIDs, each corresponding to a species, so as to approximate the module of the modified FID signal $\tilde{s}(t)$. The selected elementary FIDs as well as the coefficient associated therewith to best reconstruct the module of the modified FID signal $\tilde{s}(t)$ give information on the nature and the quantification of the species present in the sample. It should be noted here that even though such step of quantifying is carried out in the time domain, it is often recommended to execute a Fourier transform in order to be able to view the result.

According to one embodiment, during the step of identifying and/or quantifying the species to be characterized from the module of the modified FID signal $\tilde{s}(t)$, a Fourier transform is applied to a signal comprising at least the module of the modified FID signal $\tilde{s}(t)$.

According to one embodiment, during the step of acquiring, a plurality of complex FID signals S(t) is acquired.

According to one embodiment, the step of calculating the module of the modified FID signal $\tilde{s}(t)$ is performed for each modified FID signal $\tilde{s}(t)$.

According to one embodiment, after the step of calculating the module of the modified FID signal $\tilde{s}(t)$ for each complex FID signal S(t) and before the step of identifying and/or quantifying the species to be characterized, a summation of the modules of the modified signals $\tilde{s}(t)$ may be executed so as to obtain a combined FID signal. Advantageously, the step of identifying and/or quantifying the species to be characterized comprises applying a Fourier transform to said summation.

According to one embodiment, the antennas are coils and the complex FID signals S(t) acquired are delivered by different coils and during the step of acquiring, complex FID signal S(t) delivered by several voxels of the sample are acquired. A step of spatial filtering is carried out after completing the calculation of the module of the modified FID signal $\tilde{s}(t)$ for each voxel.

According to another aspect, the invention also relates to a computer program product comprising instructions, which, when executed by at least one processor, execute the following steps:

receiving one or more complex free induction decay (FID) signal(s), with each complex FID signal comprising a real part and an imaginary part, such that, in each complex FID signal, the amplitude of the signal of the reference species is at least twice greater than the amplitude of that of the at least one species to be characterized, for each complex FID signal calculating the module of each complex FID signal or calculating the module of the modified FID signal $\tilde{s}(t)$.

In another embodiment, the invention relates to a nuclear magnetic resonance (NMR) spectroscopic system for at least one sample comprising at least one species to be characterized and a reference species taken from a solvent, with the content of the reference species in the sample being at least greater than twice the value of the at least one species to be characterized. The system comprises at least one antenna so configured as to acquire 310 one or more complex free decay induction (FID) signal(s) in the time domain, with each complex FID signal being generated by applying at least a field B0 to the at least one sample and comprising a real part and an imaginary part, characterized in that the system comprises processing means so configured as to calculate the module of each complex FID signal for each complex FID signal.

Optionally but advantageously, the system according to the invention may also have at least any one of the following optional characteristics which may be taken alone or in combination:

The system also comprises means for applying the constant field B0 to the sample and means for applying a field generating an electromagnetic excitation in the constant field B0.

According to one embodiment, the antennas are coils and the acquired complex FID signals S(t) are delivered by different coils, with the system processing means being so configured that:

during the step of acquiring, complex FID signals S(t) delivered by several voxels of the sample are acquired, a step of spatial filtering is executed after calculating the module of the modified FID signal š(t) for each voxel.

According to one embodiment, the system comprises processing means so configured as to perform the above-mentioned steps and making it possible to complete the calculation of the module of the modified FID signal š(t).

According to one alternative embodiment, the system comprises processing means so configured as to execute the steps of subtracting 1351 the module of the complex FID signal S(t) from the module of the modified FID signal š(t) and then subtracting 1354 the result obtained in the previous step from the module of the modified FID signal š(t).

According to one alternative embodiment, the system comprises processing means so configured as to execute the steps of applying a Fourier transform to the module of the complex FID signal S(t) and to the module of the modified FID signal š(t); then subtracting the spectrum of the module of the signal S(t) from the spectrum of the module of the modified FID signal š(t); then subtracting the result obtained in the previous step from the spectrum of the module of the modified FID signal š(t).

In the present invention, the term antenna refers to any type of electromagnetic waves receiver.

According to another embodiment, the invention relates to a method for nuclear magnetic resonance analysis (NMR) of at least one sample comprising at least one species to be characterized and a reference species taken from water or a solvent, with the content of the reference species in the solvent being at least greater than twice the content of the at least one species to be characterized. The method comprises the following steps of:

a. applying at least one constant field $B_0$ to the at least one sample, b. acquiring, by one or more antenna(s) one or more complex free induction decay (FID) signal(s) S(t), with each FID complex signal S(t) comprising a real part and an imaginary part; with the acquisition step being performed so that, in each complex FID signal S(t) the amplitude of the signal of the reference species is at least twice greater than the amplitude of that of the least one species to be characterized;

c. for each complex FID signal S(t) calculating the module of each complex FID signal S(t)

d. optionally applying a Fourier transform to a signal taking into account the FID module, with such step being optional.

All the above-mentioned characteristics may be combined with this embodiment.

According to another embodiment, the invention relates to a method analyzing, using nuclear magnetic resonance, at least one sample comprising at least one species to be characterized and a reference species, the content of which in the sample is greater than twice the content of the at least one species to be characterized, with the method comprising the following steps:

a. applying at least one constant field $B_0$ to the at least one sample, b. acquiring, by one or more antenna(s) one or more complex free induction decay (FID) signal(s) S(t), with each FID complex signal S(t) comprising a real part (140) and an imaginary part (150);

characterized in that the method also comprises at least the following steps of:

c. obtaining a FID spectrum S(ω) by applying a Fourier transform to the real and complex parts of the at least one complex FID signal S(t), with the FID spectrum S(ω) obtained then comprising the reference species and the species to be characterized and having two portions (UFR, DFR) each extending from the resonant frequency of the reference species ($F_{ORef}$) respectively on either side of $F_{ORef}$, with the frequency of the species to be characterized being located on a first portion of the spectrum taken among said two portions (UFR, DFR);

d. modeling the signal of the reference species Sref(t) from the real and complex parts of the at least one complex FID signal S(t);

e. obtaining a spectrum Sref(ω) of the reference species by applying a Fourier transform to the modeling of the signal of the reference species Sref(t), with the spectrum Sref(ω) of the reference species then having two spectrum portions extending from the resonance frequency of the reference species ($F_{ORef}$) of the spectrum Sref(ω) and extending respectively on either side of $F_{ORef}$;

f. obtaining a modified FID spectrum $\tilde{S}(\omega)$, by substituting a second portion of the FID spectrum S(ω), with said second portion being the portion taken from said two portions (UFR and DFR) of the spectrum S(ω) and which does not comprise the species to be characterized, by the portion of the spectrum Sref(ω) taken from the two portions of the spectrum extending from $F_{ORef}$, of the spectrum Sref(ω) and extending on the same side as said second portion of the spectrum S(ω);

g. applying an inverse Fourier transform to the modified spectrum $\tilde{S}(\omega)$ to obtain a modified FID signal š(t) in the time domain;

h. calculating the module of the modified FID signal š(t).

All the above-mentioned characteristics can be combined with this embodiment.

According to another embodiment, the present invention relates to a computer program product or a non-transient computer-readable media comprising instructions, which, when executed by at least one processor executes at least the steps c. to h. of the method of the preceding paragraph.

BRIEF DESCRIPTION OF THE FIGURES

The purposes, objects as well as the characteristics and advantages of the invention will better emerge from the detailed description of an embodiment thereof which is illustrated by the following appended drawings wherein.

The appended drawings are given as examples and are not restricting the invention.

DETAILED DESCRIPTION OF THE INVENTION

Figure 1:
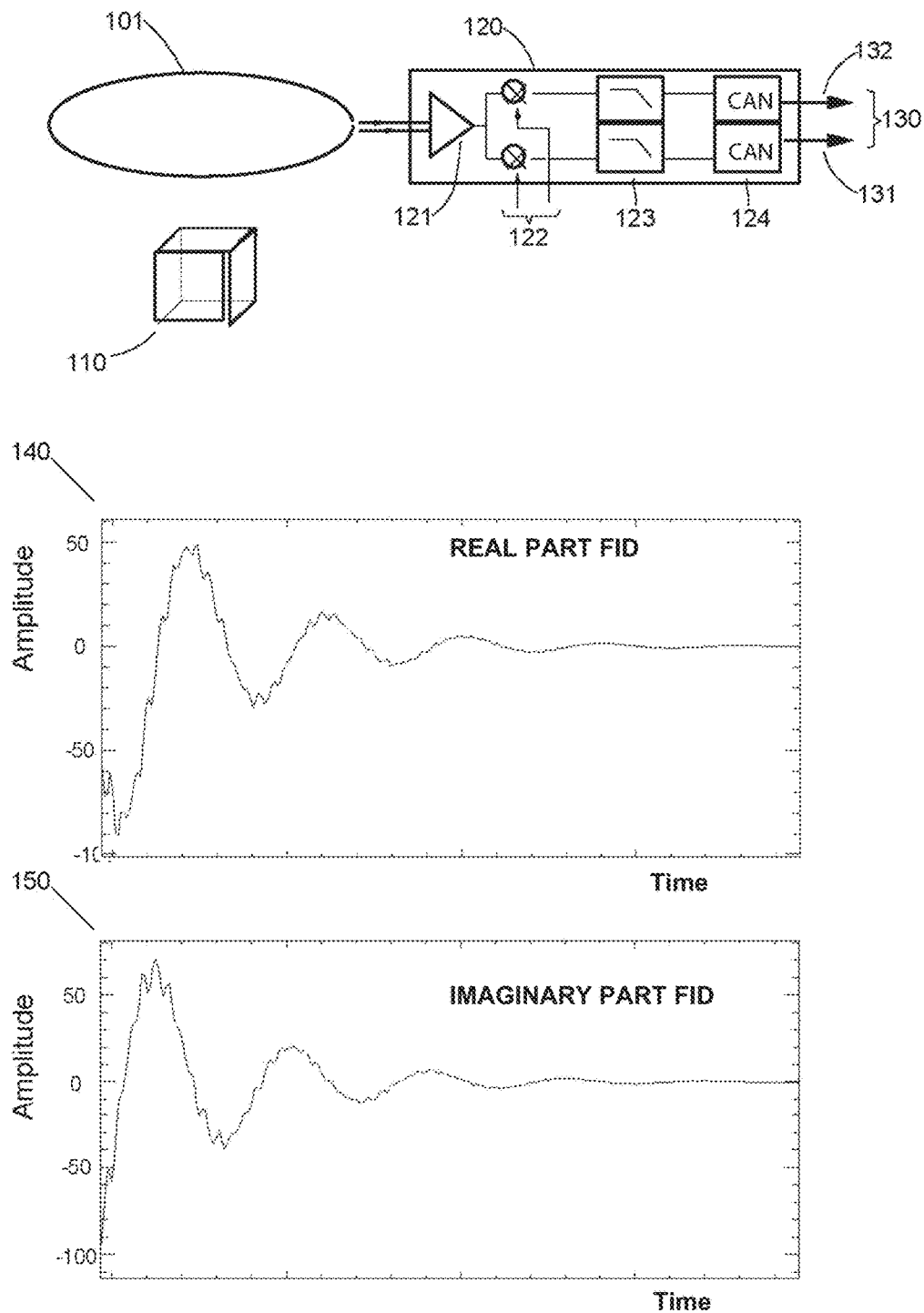
FIG. 1 briefly describes the type of FID signals detected by any antenna of known NMR equipment.

FIG. 1 briefly describes the type of signals detected by any antenna of NMR equipment. The signal may be observed after each emission of an electromagnetic pulse B1 used to disturb the hydrogen nuclei, or protons which are steady in the constant magnetic field B0. As seen above, the RF frequency used should preferably be resonating with the Larmor frequency of protons for the intensity of the magnetic field B0 developed by the NMR equipment considered and which is all the higher as the field B0 is great. As mentioned above, it grows by 42 MHz per Tesla.

The detected NMR signal is called a FID (for "free induction decay") signal. It is representative of the return to a steady-state of the nuclei after the electromagnetic disturbance which they are subject to has ceased. Using conventional means which are not described and which are not necessary for understanding the invention, the captured FID signal is delivered by an elementary volume unit of the area covered by the antenna 110. Such elementary entity is called a voxel 110. The physical size of a voxel depends on the volume resolution of the NMR equipment used.

The signal captured by the antenna is conventionally processed by an electronic receiver 120 mainly comprising an analog amplifier 121 and two analog-to-digital converters (ADCs) 124. As a matter of fact, after amplification, a frequency conversion and a quadrature detection of the FID analog signal captured by the antenna 122 is conventionally carried out from signals offset by 90°. The frequency conversion is intended to transpose the FID signal into a frequency range compatible with the operation of the following ADCs. After filtering 123, a complex signal having a so-called "real" and a so-called "imaginary" portion is thus obtained for each antenna. The two real analog electrical signals thus obtained are then each sampled by an ADC 124 so as to have a complex FID signal in a digital form 130 having a "real" component 132 and an "imaginary" component 131, i.e. in quadrature with the real part. Typically, for each captured FID signal, the number of digital samples which are available for each channel is of the order of $2^{10}$ i.e. 1024 samples. The digital signal 130 is thus liable to be processed using all the software and material resources that have been developed for decades for the digital processing of analog signals. Such resources more particularly comprise specialized digital, so-called "signal processors" and specific algorithms specifically those for implementing the Fourier transforms which make it possible to execute a spectral analysis of the received time signals.

The diagrams 140 and 150 show, in analog form, the two components of an exemplary FID signal. These are, respectively, the real part and the imaginary part of a FID signal captured by the antenna after amplification, conversion and quadrature detection of the signal.

As a first approximation, the FID signal is a simple decreasing exponential function. As a matter of fact, as the FID signal can be affected by many external sources, the fact of introducing amplitude depending on time makes it possible to make no assumption about the shape thereof. As regards the mathematical calculation, each antenna signal is thus a complex expression which is a function of time (t) of the form: $A(t)=A_0(t)e^{j(\omega t+\varphi)}$ where $\omega$ is the water resonance frequency and $\varphi$ the phase distortion.

The example in FIG. 1 shows the simple case of a single acquisition of the FID signal from a single antenna. Indeed, it is assumed in this simple example that the captured signal has sufficient amplitude to be processed after a single acquisition and that it is not necessary to carry out several successive acquisitions to improve the SNR as will be seen in some of the cases described below.

It may be noted here that if the patient moves during the acquisition of a FID then there is a change in frequency and phase between the beginning of the FID and the end of the FID which may cause a modification in the form of the lines after the Fourier transform and could reduce the accuracy of the results obtained with the method according to the invention. This is unlikely, in practice, because time for acquiring a FID is a few milliseconds. On the contrary, if the patient moves between the time the frequency was adjusted and the time the acquisition of the FID (from 1 to several seconds) is started, this is the case described below.

It should also be noted that the water signal is normally "resonant", i.e. the receiver conversion frequency is adjusted exactly on the resonance frequency of the water signal.

When this adjustment is correct, the water signal actually appears as a decreasing exponential function. When this adjustment is not correct, the frequency of the water signal is slightly different from the conversion frequency. This results in an oscillation of the FID signal. The decreasing exponential function is then modulated by a sine wave the frequency of which is equal to the difference between the frequency of the water signal and the receiver frequency conversion. The oscillation of the FID signal of FIG. 1 shows the frequency offset. A exactly "resonating" acquired signal would be similar to the one on the diagram 222 of FIG. 2. As regards the signal phase, it is arbitrary because the phase of the received FID signal is completely independent of the phase of the receiver conversion signal. The frequency conversion in the receiver is obtained by subtracting a signal having a frequency equal to the Larmor frequency from the FID signal. But the receiver does not know the phase of the FID signal. A random offset therefore necessarily occurs between the phase of the signal used by the receiver and the phase of the water signal. This is shown in the figure by the fact that the first point of the FID is generally not real. The coordinates of such first point in the complex plane are, in this example approximately (−60, −100), if reference is made to the diagrams 140 and 150. If the signal were really in phase, the coordinates of this point would be (116.0) i.e. 116 for the real part, and 0 for the imaginary part.

Figure 2:
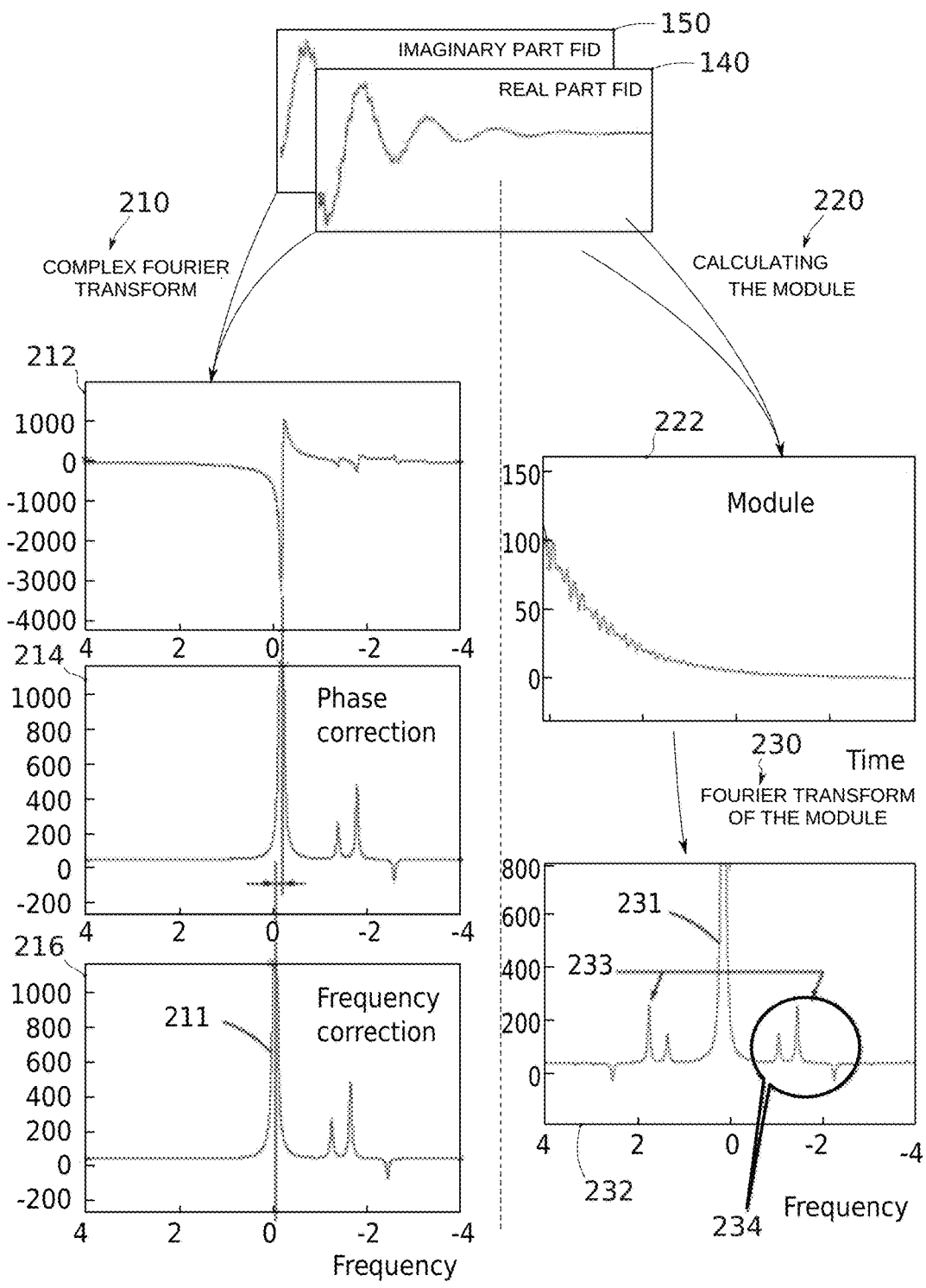
FIG. 2 compares, from the case of a single antenna and a single acquisition of a FID signal, the method of the invention and the conventional processing of the FID signal.

FIG. 2 compares, from the case of FIG. 1, i.e., the one of a single antenna and a single signal acquisition, the method of the invention and the conventional processing of the FID signal.

As seen in the previous figure, the signal captured by an antenna has a real part 140 and an imaginary part 150. The conventional processing of the FID signal is therefore performed in the complex plane. The corresponding Fourier transform 210, which makes it possible to switch from the time domain to the frequency domain and to obtain a spectral analysis of the received signal reflects the frequency and phase shifts 213 possibly present in the complex signal 130, thus obtaining the frequency spectrum 212 to which a phase 214 and frequency 216 correction must be successively applied to return to the resonant water signal 211, i.e. set to the frequency 0 of the Fourier transform.

As mentioned in the description of FIG. 1, the complex NMR signal is obtained by shifting the phase of a portion of the received signal by 90°. However, the collected signal is real, and once all the operations have been conducted in the complex plane, for mathematical convenience, the obtained spectrum is so arranged as to be real too. To this end, the imaginary part introduced for reasons of ease of calculation is then removed. If it is assumed that the FID signal is a decreasing exponential function, narrow so-called "Lorentzian" lines are obtained such as those shown in the diagram 214. The lines of diagram 212 are a mixture of Lorentzian and dispersed lines. The phasing operation or phasing consists in recovering the Lorentzian lines in the real part and in putting the dispersed lines in the imaginary part. Once this operation is completed, the imaginary part can be put aside and work can be carried out on the real part only.

The frequency offset is the same as the one previously described in FIG. 1. In FIG. 1 it results in a modulation of the FID signal while FIG. 2 is a spectral representation thereof. The frequency offset is, in this case, as mentioned above, due to the difference between the demodulation frequency used by the receiver and the actual frequency of the water signal.

It should be noted here that it must be possible to differentiate the so-called "global" phase and frequency, as described above, from the so-called "relative" phase and frequency which correspond to a phase or frequency difference as compared to another FID signal, or to another location. If two FID signals are successively acquired, these will both have the same phase and the same global frequency since the receiver demodulation signal has not changed from one FID signal to the other one. On the contrary, if the patient has moved during the acquisition, the phase and the frequency of the second FID signal will be slightly different from the first one. This is also the case for the FID signals delivered by different voxels as in the case of a so-called CSI analysis described in FIG. 5 (a CSI analysis, the acronym for "chemical shift imaging" means the "chemical shift imaging" of the resonance frequency of the nuclei as already briefly discussed above). The phase and the frequency delivered by different voxels will be slightly different due to the variations of the field B0, but the "global" frequency and phase will be the same for all voxels.

So, two corrections will have to be made: a general one which consists in correcting the phase and frequency variations generated by the converter, then a correction of the small variations induced by the patient's movement or the changes in the field B0, FID per FID or voxel per voxel.

The invention makes it possible to execute both operations at once.

The processing according to the invention of the signal captured by the antenna starts with the calculation of the module 220 of the complex signal 130 as defined above.

In the complex expression mentioned above and which is a function of time (t) $A(t)=A_0(t)e^{j(\omega t+\varphi)}$, the term $A_0(t)$ is the module or amplitude of the complex signal. This module is independent of the frequency and the phase. From a practical point of view, the module at each moment t is thus the square root of the sum of squares of the real and imaginary parts of the FID signal at that moment, as captured and converted by the electronic module 120 associated with each antenna.

Thus, at each moment t, the module of the FID signal is defined by

Module $FID(t)=|A(t)|=(A_0(t)^2 \cdot [\cos(\omega t+\varphi)^2 + \sin(\omega t+\varphi)])^{1/2}$ As the term $[\cos(\omega t+\varphi)^2 + \sin(\omega t+\varphi)^2]=1$, the module of the FID signal(t)=$A_0(t)$.

As the disturbance phase and frequency has been dealt with, the quantification of $A_0(t)$ which is actually the purpose of the experiment can now be discussed.

The signal obtained thus corresponds, at each moment, to the FID module. It is called, in the present patent application, "FID module" or simply module.

An example of this type of signal is illustrated in diagram 222.

The Fourier transform 230 is then applied to the FID module 222 to obtain its frequency spectrum 232. As the module of the signal captured by the antenna carries no frequency or phase information, it therefore does not require the corrections 214 and 216 of the conventional processing method briefly described above to be applied thereto.

In particular, the water spectrum 231 is then always centred on the frequency 0. The spectrum of the module which is a signal having a real part only is characterized in that it is symmetrical 233. It is directly usable by the following processes which are specific to each NMR application. The invention thus eliminates the need for steps dedicated to phase and frequency corrections, with these steps usually requiring a significant processing time, often even a manual action by an operator. A sample will preferably be selected which, with a conventional solution based on a Fourier transform in the time domain, has no signal on either side of the frequency corresponding to the one of the major species.

As the spectrum of the module is symmetrical, one of the halves is generally retained. It should also be noted that the Fourier transform of the FID module is simpler especially because the amount of data to be processed is half the one that must be conventionally processed when operations are carried out simultaneously on the real parts and the imaginary parts of the captured FID signals. The processing time is thus significantly reduced which enables a real time processing without affecting users. In particular, it should be noted that working on a real signal only makes it possible to divide by 2 the occupation of the computer RAM. This enables to work on a larger data volume without slowing down the machine. Moreover, having to keep only half of the spectrum after the processing divides by four the total volume of data to be saved. The gain in computing time is effectively achieved only if the size of the data exceeds the size of the memory allocated by the computer. However, this is often the case for so-called CSI analyses, more particularly described in FIG. 5, which are executed in high resolution and involve sizes of data up to four gigabytes, i.e. $4 \times 10^9$ bytes.

The SNR surprisingly remains perfectly satisfactory, although part of the information captured by the antennas (phase information) is eliminated when taking into account the FID module.

It should be noted here that the invention more specifically concerns NMR applications which relate to the analysis of secondary peaks 234 which appear in the spectral decomposition and which are generated by metabolites possibly present in the examined tissues. The water making up the major part of the tissue generates a signal with very high amplitude 231 which acts as a carrier and as a reference for the secondary peaks 234 which are to be detected and which are specific, in the considered voxel, of the presence of metabolites. These create a "chemical shift", i.e. a term used in the English literature on these subjects to qualify a "chemical offset or shift" of the precession frequency of the resonant nuclei. The frequency shift or offset appears in the spectral decomposition in the form of staggered secondary peaks which indicate the presence of such metabolites. The frequency offset is characteristic of the nature of the metabolite. The peak area, relative to that of water, makes it possible to quantify the concentration thereof in the examined tissue.

Figure 3:
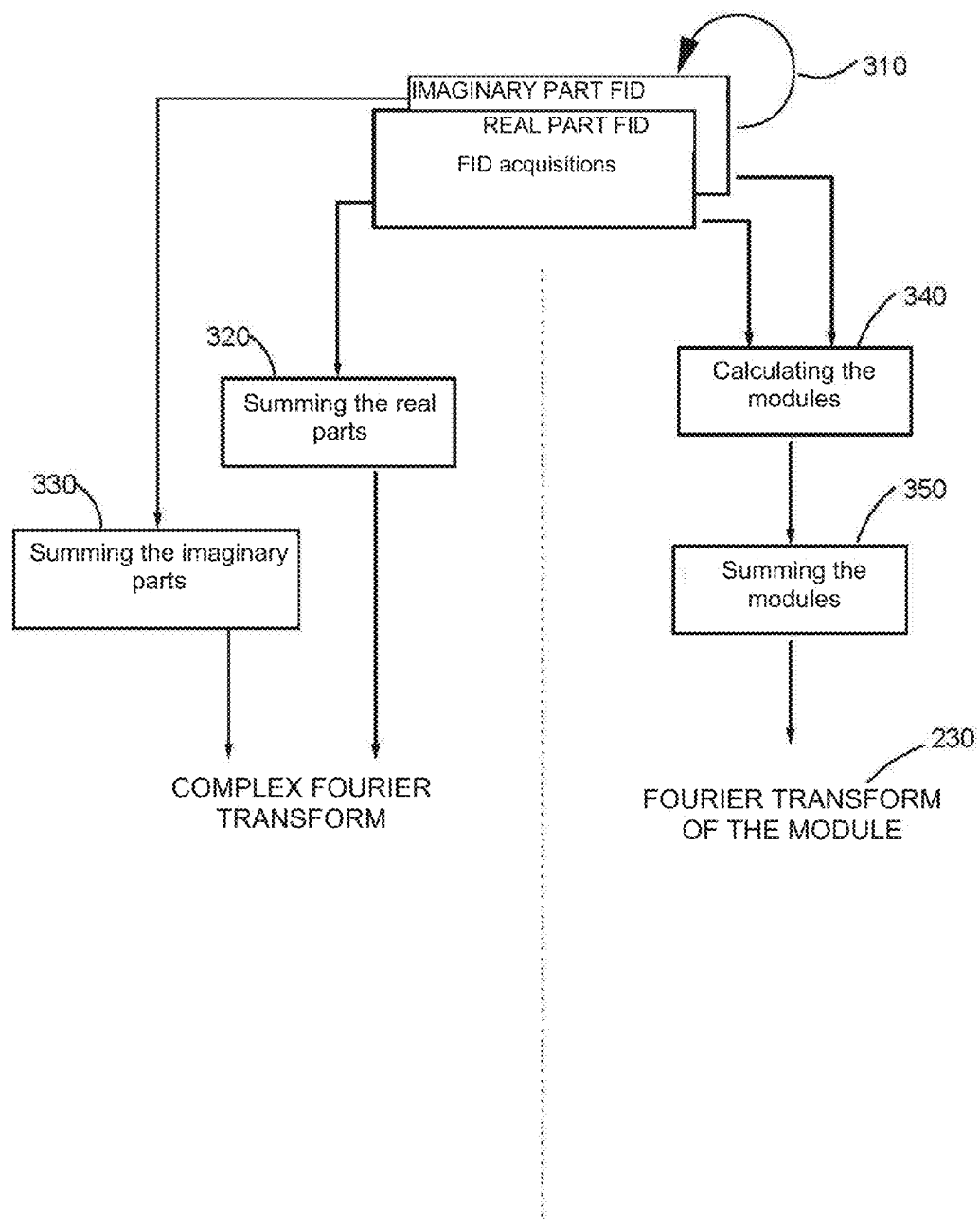
FIG. 3 illustrates the case where several acquisitions are successively performed to obtain a FID signal having a sufficient SNR to be operated.

FIG. 3 illustrates the case where several successive acquisitions 310 are necessary to obtain a FID signal having a sufficient SNR to be operated by the application.

The conventional processing, and processing according to the invention, of the FID signal are essentially identical to what is described in FIG. 2. The only differences concern the steps of summation. In the conventional processing, the real 320 and imaginary 330 parts of the successive FID signals captured should be separately summed. On the contrary, in the processing according to the invention, the module 340 of each FID signal is first calculated. Only the FID modules then need to be summed 350 before the Fourier transform 230 is applied to the resulting module, which substantially simplifies the calculation process in the case of the invention. In this case the summation is performed on phased signals aligned relative to each other, unlike the conventional case. This provides an optimum SNR.

Figure 4:
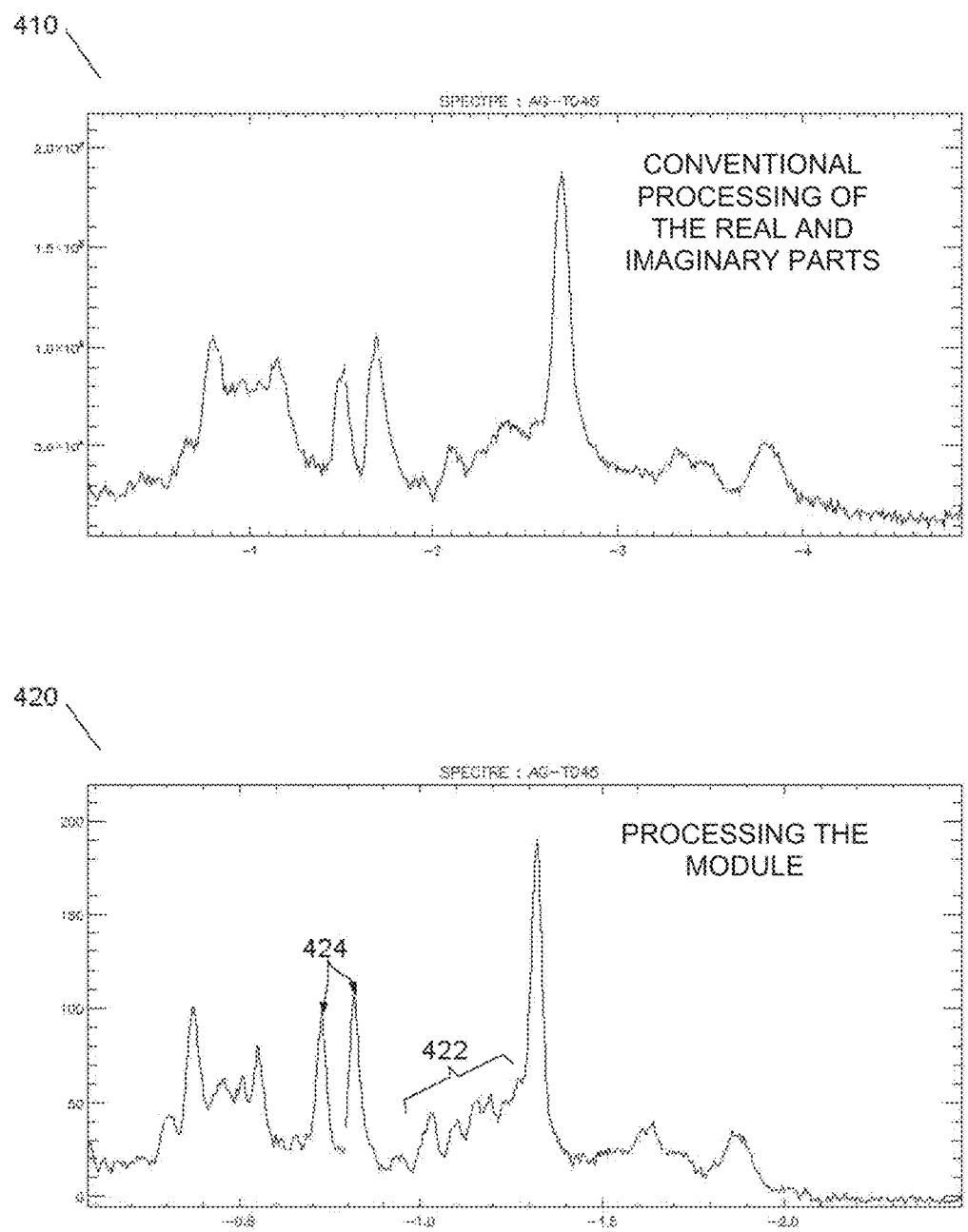
FIG. 4 compares experimental results that illustrate the advantage of using the module for the processing of the FID signals.

FIG. 4 compares experimental results which illustrate the advantage of using the module 420 for the processing of FID signals instead of using the conventional separate processing of the real and the imaginary parts 410.

FIGS. 410 and 420 focus on the interesting part of each spectrum i.e. they only show parts relating to the metabolites. The water signal and the symmetrical volume signal have been removed so as to make the region 422 of the spectrum more visible.

The diagram 420 shows that the module processing significantly improves the SNR of the captured FID signal and reduces the width of the spectrum lines. In particular, as shown in this example, the reduction in the width of the lines reveals some small secondary resonances 422 which were not visible in the conventional spectrum. The invention thus makes it possible to detect species which were hardly detectable or even non-detectable with the solutions of the prior art. The shape of the resonances 424 is also improved.

It is known that the correction of the phase and the frequency shift or offset of each FID, shown in FIG. 2, prior to summation, should improve the width of the spectrum lines and the SNR. In practice this correction is however never executed because of the difficulty met in finding the phase and frequency of each FID in real time before summation. Using the module of the FID signal as in the invention is thus a fast, simple and robust way of correcting the effect of the movements of the target which are the main origin of the phase and frequency shifts observed upon acquiring the FID signals.

Figure 5:
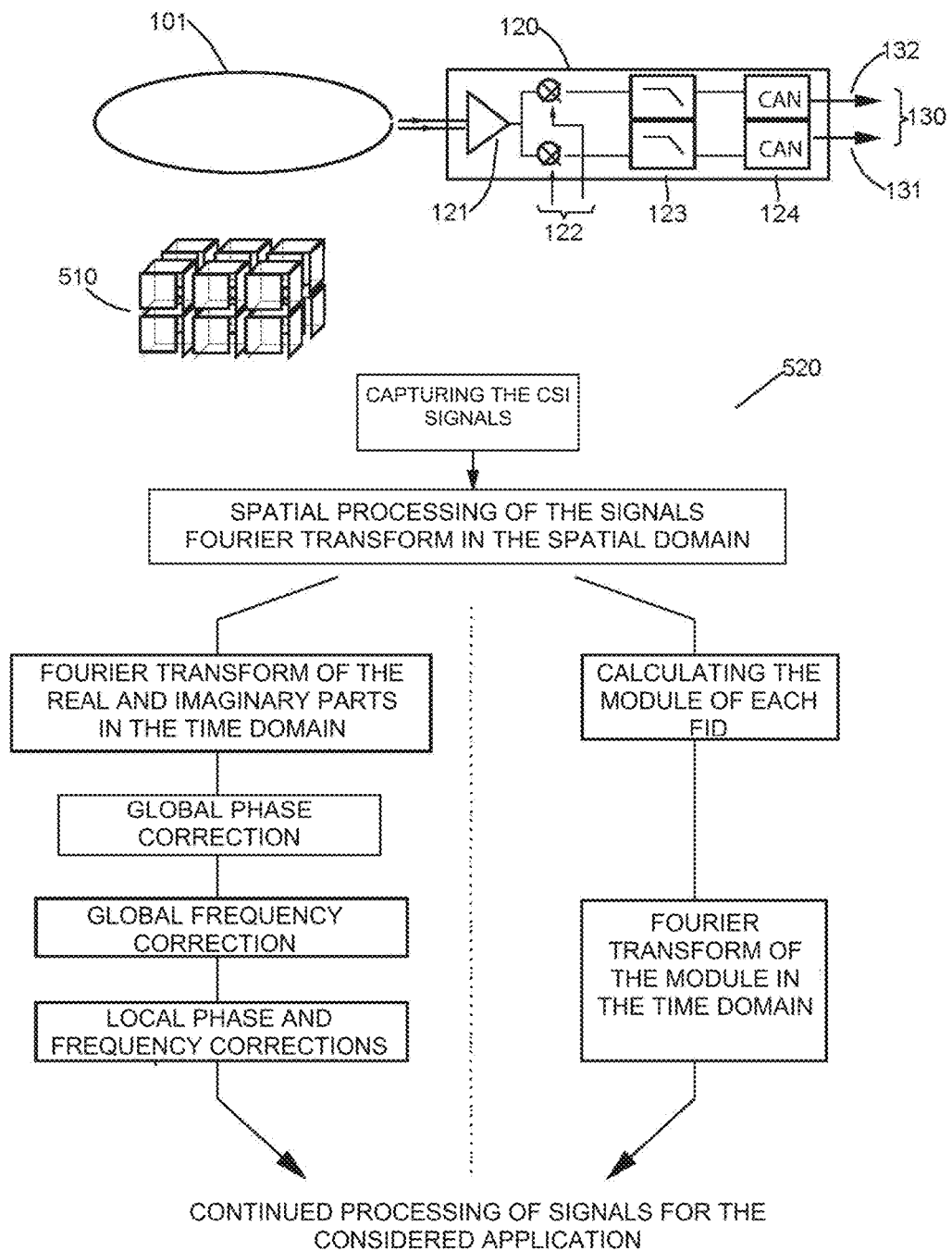
FIG. 5 illustrates the case where a spectroscopic image of a volume of tissue comprising a plurality of voxels is acquired.

FIG. 5 illustrates the case where a spectroscopic image of a volume of tissue comprising several voxels is acquired. This type of CSI analysis is conventionally executed by superimposing magnetization gradients to the fixed magnetization B0 so as to perform a spatial discrimination of the signals delivered by each voxel. This case is similar to the one shown in FIG. 1 but relates to a volume of voxels 510 wherein phase and frequency shifts due to inhomogeneities of the magnetic field B0 can be seen.

It should be noted here that whatever is done in the spatial domain is identical to what is conventionally done in NMR imaging. A Fourier transform is executed to switch from the signals encoded by the magnetic field gradients to the spatially resolved signals as it is used to switch from one FID signal to the spectrum thereof. The Fourier transform which converts the FID signal into a spectrum works on a time signal and transforms it into a frequency signal, which explains the name time (or frequency) TF. The Fourier transform which transforms the signals encoded by the gradients into an NMR image works in the spatial dimension. This processing is specific to a CSI analysis and is carried out upstream, even before the invention is applied. FIG. 5 shows that the technique of the invention is compatible with that of CSI analyses.

As seen above, the global corrections are those executed on all FID signals, identically. This mainly relates to the frequency and phase offsets between the receiver demodulation signal and the actually acquired signal. The local or relative corrections are the ones which relate to the phase and frequency differences noted between two acquired FID signals, either delivered by two different coils or successively delivered by the same coil or still if the FID signals are delivered by spatially different regions. Depending on the case, the differences noted are caused by: a patient's movement, the coil electronics, the spatial variations in the field B0s or a combination of these phenomena.

Figure 6:
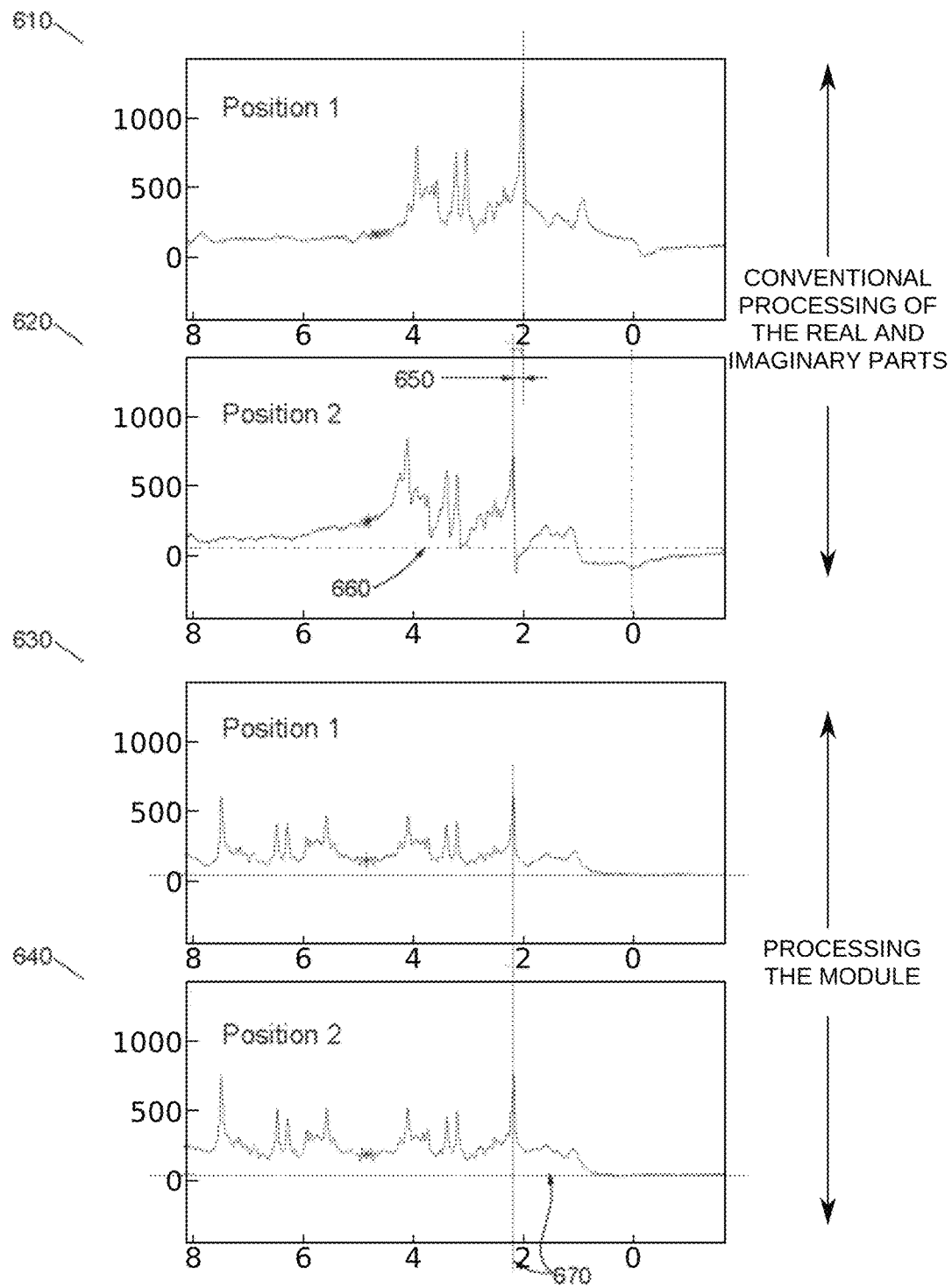
FIG. 6 compares experimental results obtained for two voxels located at different positions in a human brain.

FIG. 6 compares experimental results obtained under the conditions described in the previous figure for two voxels located at different positions in a human brain.

The diagrams 610 and 620 on the one hand, and 630 and 640 on the other hand, respectively describe the signals obtained for two voxels at different positions (1 and 2) with a conventional processing of the captured FID signals and a processing of their modules according to the invention.

It should be noted that the frequency 650 and phase 660 offsets that appear in the conventional processing of the captured signals no longer appear 670 in the processing of the module, which significantly improves the quantification thereof.

It should be noted here that, in the case described in FIGS. 5 and 6 above, i.e. the acquisition of CSI signals, multiple acquisitions may also have to be executed to improve the SNR. The invention will also apply, as described above, and particularly as described in FIG. 3 with a summation of the FID modules.

Figure 7:
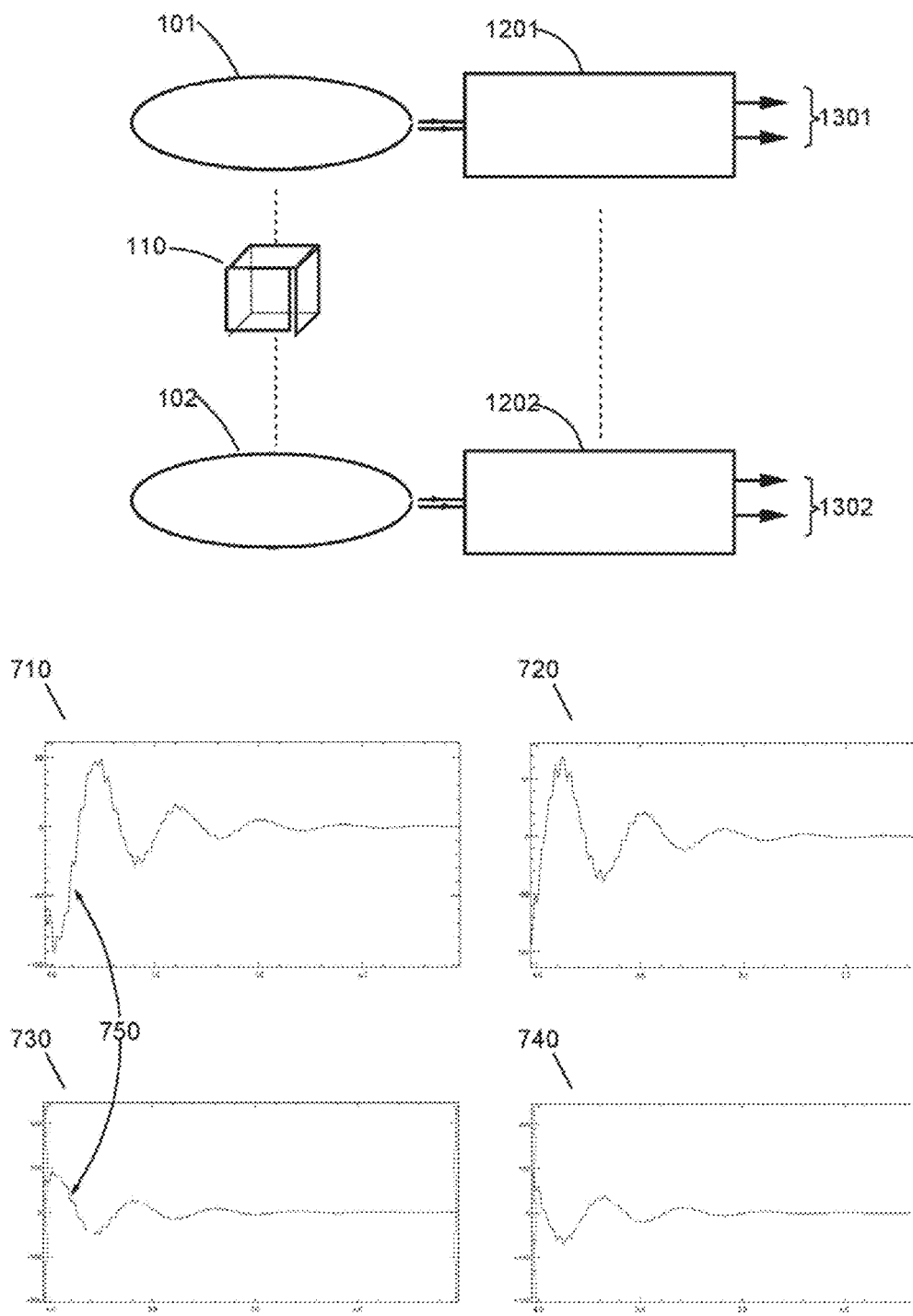
FIG. 7 illustrates the case where the FID signals are acquired from an antenna array.

FIG. 7 illustrates the case where the FID signals are acquired from an antenna array as discussed in the section on the state of the art. The invention is particularly advantageous in this complex case where the significant differences, more particularly relating to phase, which may exist between the individual antennas, must also be easily corrected.

In this case, the FID signal emitted by each voxel 110 is captured by several antennas. Two antennas 101 and 102 are shown in this example. A larger number thereof are commonly associated, for example eight-antenna networks are frequently used. Each individual antenna has its own receiving system, 1201 and 1202 in this example, each delivering a complex FID signal, 1301 and 1302.

The diagrams 710 and 730 on the one hand, and 720 and 740 on the other hand are respectively examples of the real parts and imaginary parts of the complex FID signals delivered by each of the antennas. As expected, significant differences 750 in the phase and amplitude of the signals captured by the individual antennas of the antenna array can be noted.

It should be noted here that a global phase and frequency shift exists which is common to all individual antennas in the array, however the individual differences in phase and amplitude between the antennas must always be compensated as will be seen hereafter.

Figure 8:
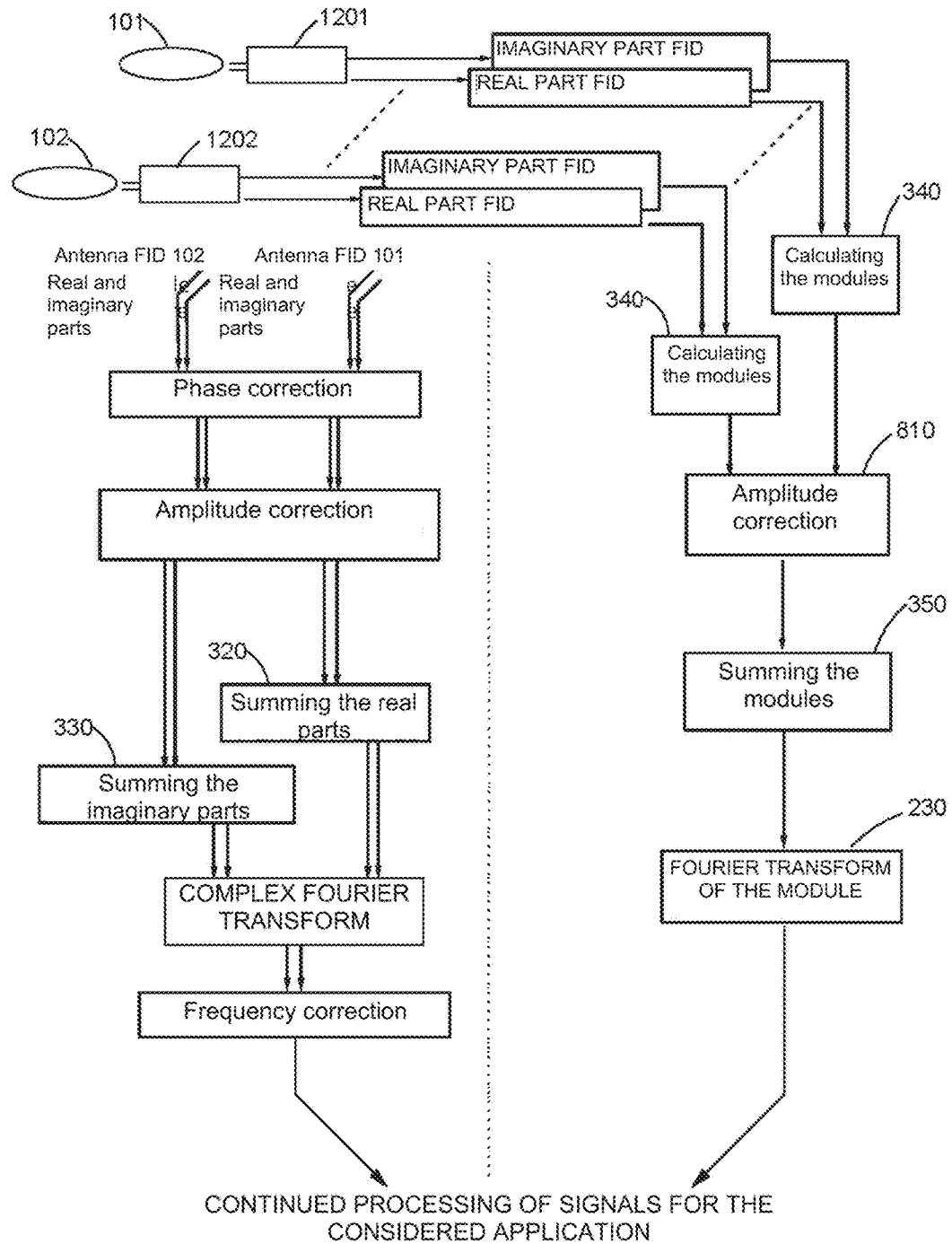
FIG. 8 illustrates the steps of the method of the invention for processing the FID signals captured from an antenna array and compares same to those of a conventional processing.

FIG. 8 illustrates the steps of the method of the invention for processing FID signals captured from an antenna array and comparing same to those of a conventional processing thereof.

The method of the invention is extremely simple and is not significantly different from what is described in FIG. 3 for the subsequent acquisition of FID signals from a single antenna. In the case of FIG. 8 the signals are acquired, preferably simultaneously, and a module 340 is calculated for each of the signals acquired from the individual antennas 101 and 102 in this example. Multiple acquisitions in the case of an antenna array are of course not excluded, as in FIG. 3.

A notable difference, in the case of an antenna array, is that, during the next step 810, a correction of the amplitude of the modules delivered by different antennas is required so as to take into account all the inevitable differences between the individual antennas of the array.

A method for applying the correction of the amplitude consists in performing a weighting of each FID signal. A weighting factor may for example be applied, for each FID module, to the coil by which it has been delivered, with this weighting factor being equal to the square of the module FID at the time t=0 divided by the sum of the squares of the modules of each FID at time t=0.

The summing 350 of the modules, the amplitude of which has just been weighted, is then executed. The spectral composition of the module resulting from the combination of the FID signals can then be calculated using a Fourier transform 230.

It should be noted that the weighting of the FID signals, though preferable, is optional only.

By comparison, the much more complex conventional process is on the left side of FIG. 8. This part should also be compared with FIG. 2, which concerns only a FID signal. It should be noted here that, in the case of FIG. 2, the phase correction can be indifferently carried out before or after the Fourier transformation since there is only one FID signal. It is traditionally carried out manually after the Fourier transform as it is easier to visualize the phase variations on the spectrum than in the FID signal. In the case of FIG. 8, this correction is executed beforehand, since the signals of the different coils are firstly recombined prior to the processing. However, executing the Fourier transform of each signal of each coil, then the phasing and the summing thereof could also be envisaged. However, as many Fourier transformations as there are coils should be executed, for example 64 if 64 coils are used.

Figure 9:
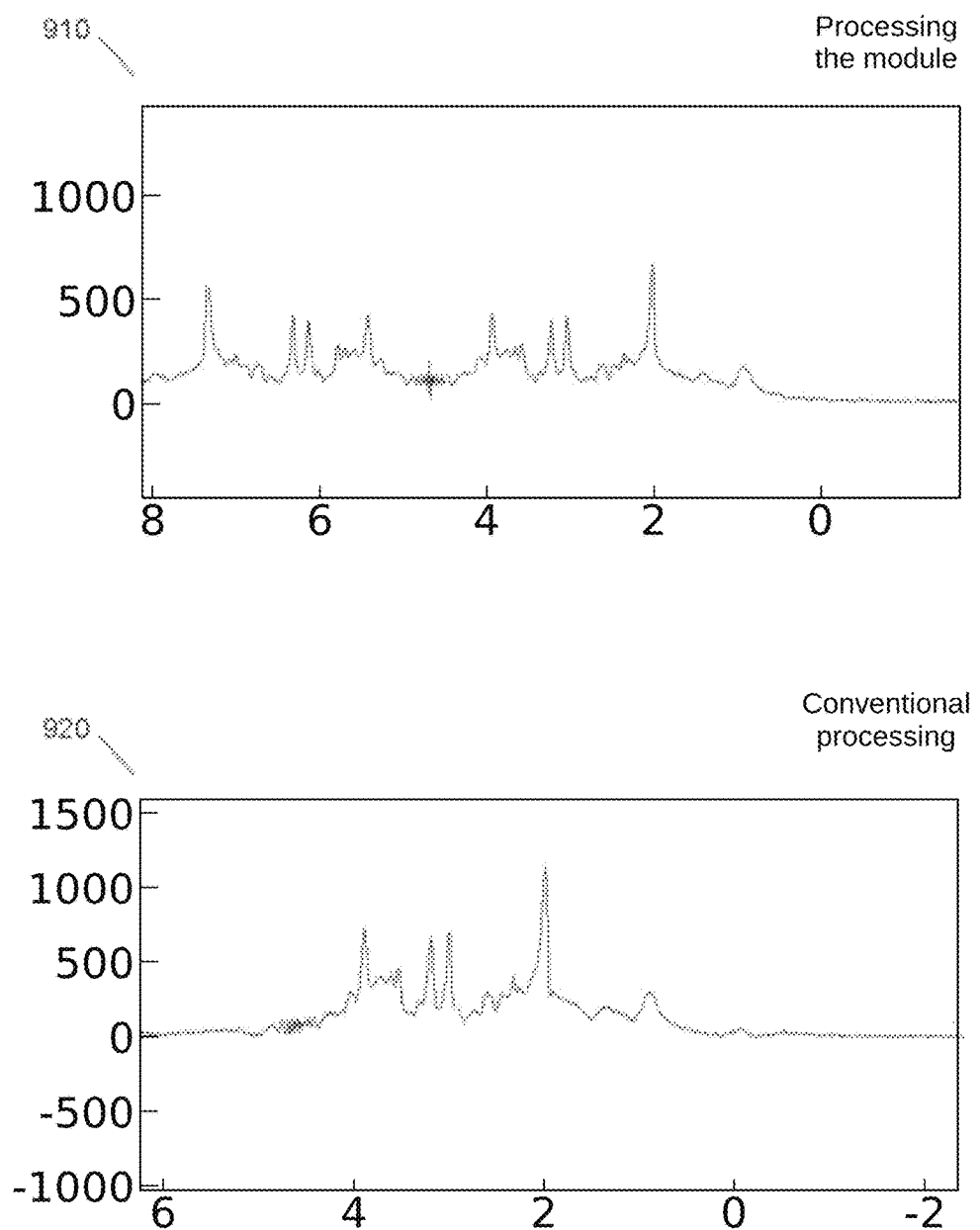
FIG. 9 compares experimental results obtained from an antenna array.

FIG. 9 compares experimental results obtained from an antenna array under the conditions described in the previous figure.

The diagrams 910 and 920 show the spectra obtained after acquiring and summing the FID signals, the Fourier transformation and the elimination of the line of water in these examples, so as to better visualize the metabolites. Diagram 920 shows the real part of the spectrum obtained after the conventional processing of the FID signals. As mentioned earlier, the imaginary part is artificially introduced by the receiver and contains no additional information. It is therefore only used when processing the signals, never in the presentation of the results. The diagram 910 shows the result of the processing according to the invention of the module of the FID signal. As already mentioned, the processing of the module results in a symmetrisation of the spectrum, one half of which only is kept. The peaks in the diagram 920 obtained with the known systems are in the diagram 910 obtained with the solution of the invention. Thus, in spite of the loss of information caused by the taking into account of the module prior to summing the different FIDs, the metabolites may still be characterized. Characterizing a species usually involves identifying and/or quantifying the nature of such species in the sample. It should further be noted that the peaks thereof are very narrow, which enables an accurate characterization and shows that the signal/noise ratio is not visibly degraded by the processing of the module of the signal according to the invention.

As shown in FIG. 9, it may be advantageous to remove water to improve the acquisition of the signals from the metabolites. As a matter of fact, in the brain, the water signal is much, by approximately $10^5$ times, greater than that of the metabolites. In order to take all advantage from the whole dynamics of the analog digital converters (ADCs), the water signal is often partially or completely removed before acquiring the FID signal.

In known methods and as in the case of the result of FIG. 920, which illustrates a conventional processing, the water signal is typically eliminated in two steps. A first step is performed during the acquisition using a suitable sequence (i.e. attenuation in this case). As such suppression is never perfect, a second elimination is performed after the summation to reduce the number of signals to be processed, usually just before the quantification of the spectra. As mentioned above, the first suppression aims at reducing the amplitude of the signal received by the analog-digital converter of the receiver, and thus at keeping the full coding range, which is typically 16 bits, for digitalizing at best the smallest signals. The second step is performed to facilitate the quantification of the metabolites. For this purpose, the water signal is modelized by performing a singular value decomposition of the signal, while retaining, among the main components only those which correspond to the water signal. A signal is reconstructed from these values which are subtracted from the spectrum.

However, as already seen, the water signal is used as the phase and frequency reference signal within the scope of the invention. Water is then only partially suppressed so as to keep a signal having sufficient amplitude to be used. As already mentioned above, the water signal can also be used as the concentration reference for estimating the absolute concentrations of the metabolites. In this case the whole water signal has to be obtained. It may be necessary to perform two successive experiments, one with a partial or total suppression of water and one without such suppression, in order to reconcile the imperatives of a better visualization of the metabolites on the one hand and the quantification thereof on the other hand.

The theoretical aspects of the invention are supported by the following mathematical developments.

If A(t) is the signal acquired from a voxel having a single compound, i.e. a single species, in the absence of noise, it is expressed as shown in the equation [1] below:

$$A(t) = A_0(t) e^{j(\omega t + \varphi)} \quad [1]$$

wherein $A_0(t)$ is the waveform of the FID signal, $\omega$ is the resonance frequency of the single compound and $\varphi$ represents all the phase distortions.

One way of correcting the phase distortions consists in taking the module of the signal as shown in the equation [2] below:

$$\|A(t)\| = A_0(t) \quad [2]$$

The module also removes the frequency information and, after the Fourier transform, the result is a "resonant" signal. If it is now assumed that the single compound corresponds to the peak of water, the following expression is obtained, while using the same notation as in the equation [3] below:

$$H2O(t) = A_{H2O}(t) e^{j(\omega_{H2O} t + \varphi_{H2O})} \quad [3]$$

It should be noted here that, in these equations, the reference species is considered as being water. The invention is however not limited to water as the reference species. These equations may be used while substituting any solvent used as the reference species for water.

When another compound is added to the water signal, the module of the acquired signal becomes:

$$\|S(t)\| = \sqrt{(H2O(t) + A(t))^* (H2O(t) + A(t))} \quad [4]$$

In this expression, the character * indicates the complex conjugate. The product under the square root can be written as follows, using the equations [1] and [3], after development:

$$\|S(t)\|^2 = (A_{H2O}(t) e^{-j(\omega_{H2O} t + \varphi_{H2O})} + A_0(t) e^{-j(\omega t + \varphi)})(A_{H2O}(t) e^{j(\omega_{H2O} t + \varphi_{H2O})} + A_0(t) e^{j(\omega t + \varphi)})$$

$$= A_{H2O}(t)^2 + A_0(t)^2 + A_0(t) A_{H2O}(t)(e^{-j(\omega_{H2O} t + \varphi_{H2O})} e^{j(\omega t + \varphi)} + e^{j(\omega_{H2O} t + \varphi_{H2O})} e^{-j(\omega t + \varphi)})$$

$$= H_{H2O}(t)^2 + A_0(t)^2 + A_0(t) A_{H2O}(t)(e^{j((\omega - \omega_{H2O})t + \varphi - \varphi_{H2O})} + e^{-j((\omega - \omega_{H2O})t + \varphi - \varphi_{H2O})})$$

$$= A_{H2O}(t)^2 + (A_0(t)^2) + 2 A_0(t) A_{H2O}(t) \cos((\omega - \omega_{H2O})t + \varphi - \varphi_{H2O})$$

If the terms $\Delta\omega = \omega - \omega_{H2O}$ and $\Delta\varphi = \varphi - \varphi_{H2O}$ which respectively correspond to the frequency and phase shifts between the added compound and that of water are now introduced, we obtain:

$$\|S(t)\|^2 = A_{H2O}(t)^2 + (A_0(t)^2) + 2 A_0(t) A_{H2O}(t) \cos(\Delta\omega t + \Delta\varphi)$$

$$= (A_{H2O}(t) + A_0(t)\cos(\Delta\omega t + \Delta\varphi))^2 +$$
$$A_0(t)^2 - (A_0(t)\cos(\Delta\omega t + \Delta\varphi))^2$$

$$= (A_{H2O}(t) + A_0(t)\cos(\Delta\omega t + \Delta\varphi))^2 + A_0(t)^2(1 - \cos^2(\Delta\omega t + \Delta\varphi))$$

$$(A_{H2O}(t) + A_0(t)\cos(\Delta\omega t + \Delta\varphi))^2 + (A_0(t)\sin(\Delta\omega t + \Delta\varphi))^2$$

and finally the equation [5]

$$\|S(t)\| = \sqrt{(A_{H2O}(t) + A_0(t)\cos(\Delta\omega t + \Delta\varphi))^2 + (A_0(t)\sin(\Delta\omega t + \Delta\varphi))^2}$$

$$= (A_{H2O}(t) + A_0(t)\cos(\Delta\omega t + \Delta\varphi)) \sqrt{1 + \left(\frac{A_0(t)\sin(\Delta\omega t + \Delta\varphi)}{A_{H2O}(t) + A_0(t)\cos(\Delta\omega t + \Delta\varphi)}\right)^2} \quad [5]$$

Assuming that $A_{H2O}(t)$ is very large as compared to $A_2(t)$, as is the case in all the experiments where water is not suppressed, the second term of the expression may be neglected. The following expression is then obtained:

$$\|S(t)\| = A_{H2O}(t) + A_0(t)\cos(\Delta\omega t + \Delta\varphi) \quad [6]$$

The description of the invention below takes into account what the technique showed in details in the preceding figures (FIGS. 1 to 9) and which consists in using the module of the FID signal and may, for certain applications, be restrictive.

Figure 10A:
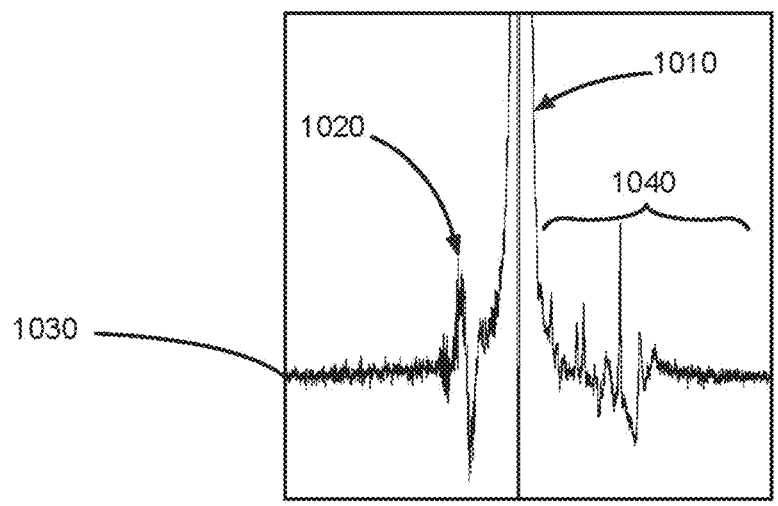
FIGS. 10a and 10b describe the artefacts aliasing resulting from the use of the module for processing NMR signals.
Figure 10B:
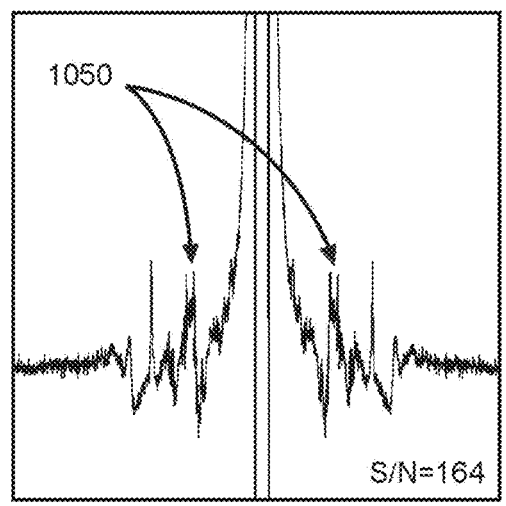

As a matter of fact, as already seen, using the module of the FID signals results in a symmetrisation of the spectrum around the frequency of the reference species, usually water 1010, so that, as shown in FIGS. 10a and 10b, the noise 1030 and the artefacts 1020, if any, which are located on the left of the spectrum are then superimposed on the signal resulting from the symmetrisation, as shown in FIG. 10b. Not only an increase in noise, but also an aliasing of the artefacts in the interesting part of the spectrum, the right one 1040 wherein the metabolites desired to be analyzed, are most commonly located, can then be noted.

The artefacts may have several causes. These reasons may include:

unwanted signals which may originate from the explored region or regions near the explored area. Such signals should be eliminated by the acquisition sequence, but this suppression may be faulty, because of, for example, the subject's movements, movements of objects around the magnet which may affect the magnetic field (opening and/or closing a door in the room, for example), poor homogeneity of the magnetic field, a variation over time in the magnetic field.

signals which are desired but which, for the same reasons as mentioned above, are shifted relative to their normal resonance frequency. For example water coming from a region where the inhomogeneity of the field results in the resonance frequency thereof being off by several Hertz relative to the resonance frequency of the explored region (the eye, the synovial fluid, . . . ) may appear as an extra resonance.

electromagnetic interferences (radio wave, wifi, . . . ) which are sensed by the NMR probe, and superimpose on the spectrum.

a spurious signal. For example, the acquisition sequences comprise many pulses and certain combinations of such pulses may create a spurious signal which superimposes on the spectrum.

As indicated above, whatever the cause of these artefacts, the latter and/or noise to the left of the water signal are found, by the symmetrisation induced by the module, superimposed on the signal on the right side of water.

Figure 11A:
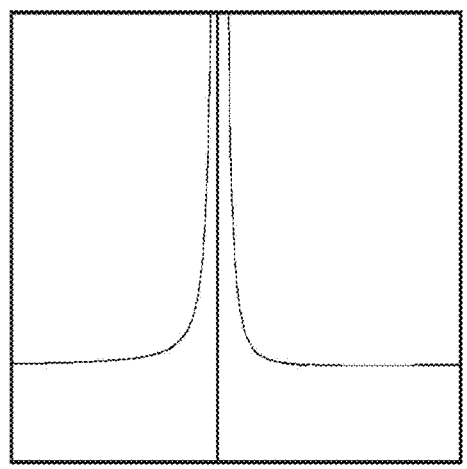
FIGS. 11a to 11c describe a method according to one embodiment of the invention, a so-called DFRR method, wherein a model of the reference species (water) is substituted for half of the spectrum.
Figure 11B:
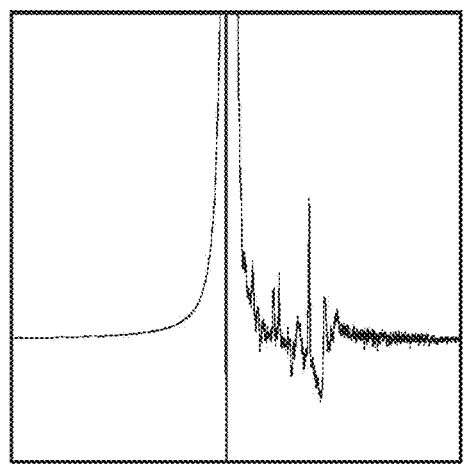
Figure 11C:
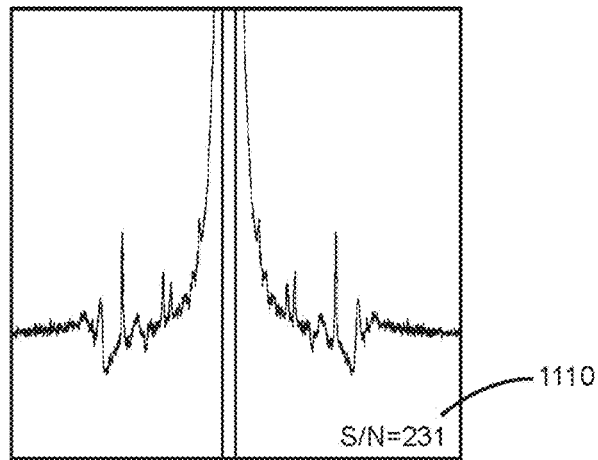

FIGS. 11a to 11c illustrate and briefly describe the solution provided by the invention to this problem.

As shown in FIG. 11a, the spectrum of water is first modelized from a sample that is desired to be characterized. This modeling will be used in the invention to substitute the corresponding portion of the model for half the acquired spectrum located on the left of the frequency of the reference species. The result shown in FIG. 11b is then obtained. The thus recomposed spectrum comprises no noise or artefact on the left side. The right side corresponds to the acquired signal comprising the species to be characterized. The following steps are identical to those which have been described previously: performing an inverse Fourier transform to return to a FID in the time domain; extracting the module of the recomposed spectrum; then returning to the frequency domain, typically using a Fourier transform, so as to obtain a final spectrum which is not disturbed by noise and any artefacts from the left side as illustrated in FIG. 11c.

It should be noted that the SNR is thus improved, as expected, by a ratio of a square root of 2 relative to the corresponding value in FIG. 10b.

In order to modelize the carrier, i.e. the signal of the reference case, several techniques may be used. One such technique is widely used in this domain, to modelize water. This modeling is then used to subtract the modelized water signal from the NMR spectrum. Such modeling technique is known as the HLSVD, the acronym for "Hankel Lanczos Singular Value Decomposition" i.e. "Hankel Lanczos' method for singular value decomposition". When applied to the present invention to modelize the signal of the reference species, the HLSVD method comprises the following main steps:

A matrix is created from the FID signal (the first line of such matrix contains the FID signal, the following lines contain the circular permutations of this FID signal, by 1 point for the $2^{nd}$ line, by 2 points for the $3^{rd}$ line, etc.)

This matrix is decomposed into eigenvalues and eigenvectors, and only 10 or 20 principal components are then retained.

Among such 10 or 20 (the choice is left to the user) major components, only those which appear at a frequency close to that of the water signal (e.g. 0.5 ppm around the position of the water signal) are retained. A FID signal is then reconstructed from such resonances. With such decomposition, the water signal, which may have an arbitrary shape, is divided into several Lorentzian lines. The sum of such Lorentzian lines reproduces the shape of the water signal.

Reference may particularly be made to the following publication concerning such modeling technique: "SVD-Based Quantification of Magnetic Resonance Signals", by PIJNAPPEL, VAN DEN BOOGAART, DE BEER, VAN ORMONDT and which was published in the "Journal of Magnetic Resonance" 97, 122-134 (1992).

Figure 12A:
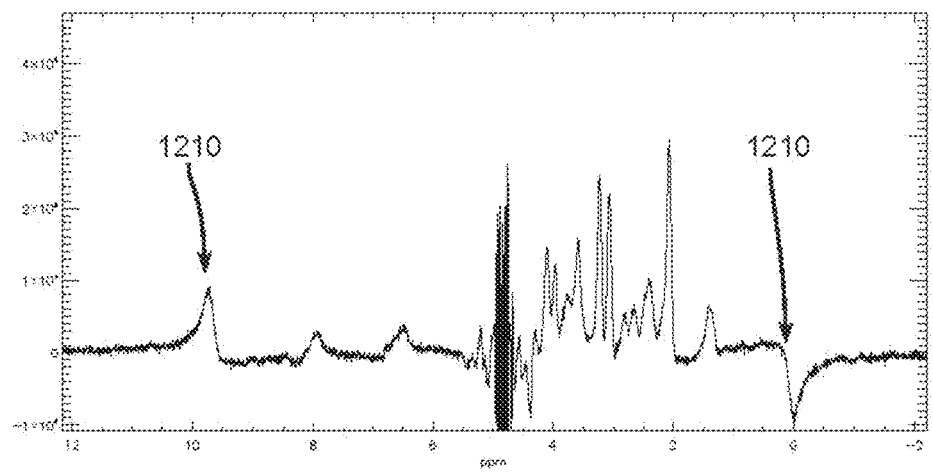
FIGS. 12a to 12f describe the processing of the antisymmetric artefacts or "sidebands", according to one particular embodiment of the invention.
Figure 12B:
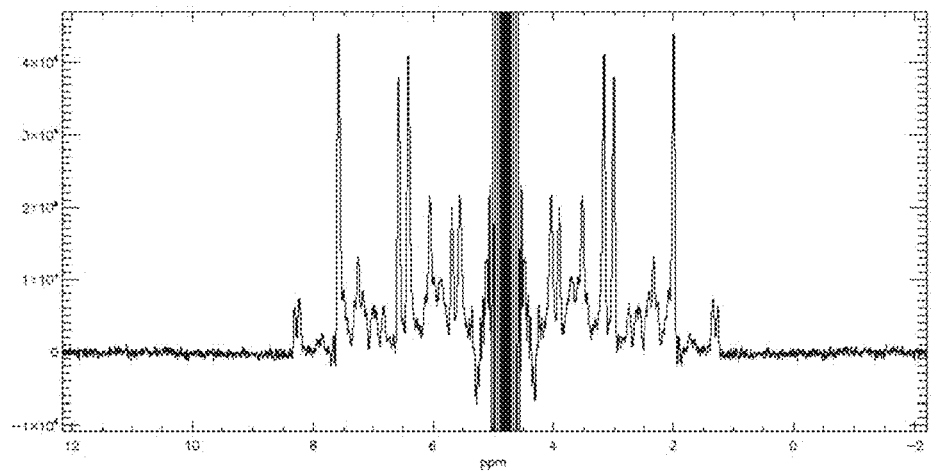

The technique described in FIGS. 11a to 11c however shows another limitation in the cases where antisymmetric artefacts are present in the captured spectrum generally called "sidebands" since they most often take the shape of peaks or side bands. Such type of artefacts 1210 is illustrated in the example of FIG. 12a. Such artefacts, in pairs, have symmetric frequencies with respect to the resonance frequency of the reference signal, equal amplitudes and opposite signs. The processing thereof using the technique described in FIGS. 1 to 9, wherein the module of the FID signals is used, results in superimposing antisymmetric artefacts in the spectral portion on the right of water. Such processing therefore leads to the automatic suppression of such type of unwanted artefacts and after such processing of the module of the signals a spectrum is indeed obtained as shown in FIG. 12b, where they no longer appear.

This advantage is of course lost when the technique briefly described in FIGS. 11a 11c, which makes it possible to reduce noise and to remove the asymmetrical artefacts 1020 of the type shown in FIG. 10a, is applied beforehand.

The following figures thus describe a complete technique which improves noise and also makes it possible to remove the asymmetrical artefacts 1210 of the "sideband" type, and asymmetrical 1020 ones.

Figure 13:
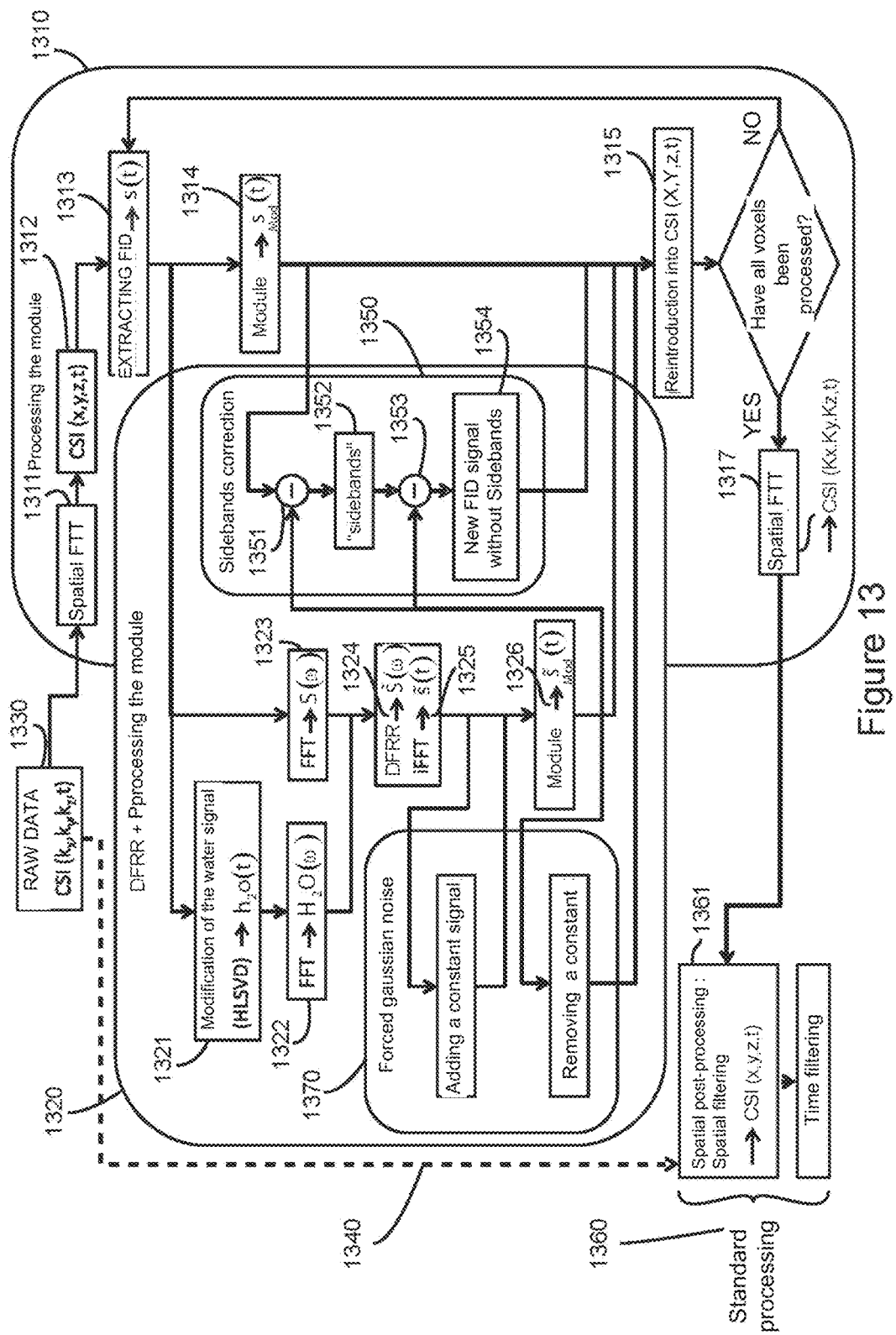
FIG. 13 is a flow chart of the steps of one embodiment of the method for correcting phase and/or frequency in FID signals according to the invention.

FIG. 13 shows in box 1310, the flow chart for the processing of the module of the FID signals as described above in FIGS. 1 to 9 which more particularly applies to a CSI type process, in this example, without this being restrictive. The steps which must be added to obtain the additional results mentioned above, i.e. improving the SNR and removing the artefacts, are comprised in box 1320. The additional processing is called hereinafter "DFRR", the acronym for "Downfield region replacement" which refers to the replacement of part of the spectrum by a model as already described briefly in FIGS. 11a 11c. Such processing can also be described as the substitution of the corresponding part of the spectrum of the reference signal for a part of the spectrum. The components of the flow chart which do not belong to such boxes are described hereafter.

From the stream of captured CSI raw data 1330, processing is applied thereto, of the Fourier transform type in the spatial domain 1311. The algorithm used is of the FFT type, the acronym for "fast Fourier transform", which is widely used for processing digitized analog signals. The FID of a first voxel S(t) is extracted 1313 from the CSI file 1312 and processed using a modeling method such as the HLSVD method mentioned above. The model of the signal of the reference species is thus extracted 1321 from the singular value decomposition by selecting the resonance within a range of plus or minus 0.5 ppm (parts per million) around the resonance of water. The signal of the reference species is designated by the generic term Sref(t). Such reference species is often water, in the example that follows, the term used for the signal of the reference species will be h2o(t). Of course, the invention applies whichever the reference species, with the latter being advantageously taken from a solvent. Usually h2o(t) is used to remove the signal of residual water and it is subtracted from the signal S(t). As regards the invention, both the FFT of S(t) and h2o(t) are calculated, which leads to obtain respectively S(ω) and H2O(ω) (the latter term referring to the spectrum of the frequency of the signal of the reference species, typically water. This term is equivalent to the term Sref(ω) which is also used in the present description, with such terms being interchangeable regardless of the embodiment, particularly in embodiments where the reference species is not water). These two steps of calculating FFT are respectively referenced 1322 and 1323 in the box 1320 of FIG. 13.

If the acquisition is executed with the signal of the resonating reference species, S(ω) can be separated into two regions: the downfield region (DFR), which is one half of the part of the spectrum located on the left of the signal of the reference species; and the upfield region (UFR) which is the other half of the part of the spectrum on the right of the resonance of the reference species. Each of these two regions extends from the resonance frequency $F_{0Ref}$ of the reference species.

Similarly, the spectrum of the water signal modelized from S(t) can be separated into two regions: the downfield region, which is one half of the part of the spectrum located on the left of the signal of the reference species; and the upfield region which is the other half of the part of the spectrum on the right of the resonance of the reference species. Each one of these two regions extends from the resonance frequency $F_{0Ref'}$ of the reference species in this spectrum, resulting from the modeling. In practice, the resonance frequency of the signal of the reference case $F_{0Ref'}$ of the modelled spectrum is equal to the resonance frequency of the signal of the reference species $F_{0Ref}$ of the spectrum comprising all the species i.e.: $F_{0Ref'}=F_{0Ref}$.

If it is now assumed that all the resonances of the metabolites of interest are located in the UFR part of the spectrum, the DFR contains only noise and artefacts. This region may therefore be replaced by the same region 1324 extracted from the model of the signal of water H2O(ω) without changing the quantification of the spectrum.

The region on the right of the reference species in the modelized signal H2O(ω) of the reference species is thus not subtracted from the signal S(ω) comprising the species to be characterized, but it replaces the DFR part of the signal S(ω). The replacement 1324 of the DFR S(ω) by the DFR of H2O(ω) leads to a new signal of the spectrum S(ω) characterized by a DFR without noise and without artefacts that can be described as follows:

$$\tilde{S}(\omega) = S(\omega) \text{ if } \omega < 0$$
$$= H2O(\omega) \text{ if } \omega > 0$$

Using H2O(ω) as a model for the DFR does not introduce a break in the new signal S(ω) as would be the case if the DFR had simply been made null or removed. The variable $\tilde{S}(\omega)$ is still continuous; its derivative is also continuous. As already mentioned, this step 1324 in the process is called DFRR. If now the inverse fast Fourier transformation (iFFT) of S(ω) is calculated 1325, a new FID $\tilde{s}(t)$ is obtained in the time domain. Then the module of $\tilde{s}(t)$ is calculated 1326 and reintroduced 1315 into the original CSI file.

This system has been preferably selected because the voxel shift technique used is based on the manipulation of the so-called k space (k-space) which is a data structure well known and widely used in NMR. The data is then reconstructed in the k-space.

Then, the standard processing 1360 can be performed as would be done on the original raw data in the case of a conventional processing which would take a direct path 1340, as provided in the state of the art.

After the step of calculating the module of the modified FID signal $\tilde{s}(t)$ and the reintroduction 1315 thereof into the CSI file, applying a Fourier transform may be omitted, according to an embodiment. The identification and/or quantification in the time domain is then carried out. In this case, well-known software allows for example to sum predetermined elementary FIDs and each corresponding to a species, so as to approximate the module of the modified FID signal $\tilde{s}(t)$. The elementary FIDs selected and the coefficient associated therewith to best reconstruct the modified module of the modified FID signal $\tilde{s}(t)$ give information on the nature and the quantification of the species present in the sample.

Alternately and preferably, after the step of calculating the module of the modified FID signal $\tilde{s}(t)$ and the reintroduction 1315 thereof into the original CSI file, a Fourier transform can be applied thereto. A spectrum is then obtained for each of the modules of the modified FID signal $\tilde{s}(t)$, with each of these spectra corresponding to a voxel.

A new composite spectrum $$\tilde{S}_{Mod}(\omega) = FFT(\| \hat{s}(t) \|)$$

is then obtained. However, the symmetrisation induced when processing the module will now mix the UFR of the original spectrum with the calculated DFR containing neither noise nor artefact. As previously described in FIGS. 1 to 9, the intensity of resonance of the metabolites is always divided by a factor of two. In this optional implementation of the invention, noise is also reduced by the same factor, which leaves the SNR unchanged. So the SNR is no longer degraded as before.

As already noted, in the presence of antisymmetric artefacts of the "sideband" type, those located in the DFR will be removed by the DFRR processing 1320. The removing of the "sidebands" in the DFR itself affects the cancellation thereof as already discussed above. The invention describes hereafter a solution to solve this problem. It is also shown that the DFRR processing may also be used without water suppression.

Although the example above is particularly advantageous when the method is applied to CSI type (i.e. multi-voxel) imaging, this method does not limit CSI imaging. As a matter of fact, it can be applied to a single-voxel processing. In this case, the method will be much the same, except for the steps dedicated to spatial processing which are then no longer necessary. The step of spatial filtering is particularly suppressed.

Besides, although the species to be characterized are most often located on the right of the signal of the reference species, the invention also applies to cases where the species to be characterized are located on the left of the signal of the reference species.

As indicated in the above description, most of the time, the species desired to be analyzed are located on the right of the reference signal. There may be species to be characterized on the left of water, but they are not usually visible in normal spectroscopy/spectrometry, as practiced in the biomedical industry. However, the invention extends to the cases where the species to be characterized are located on the left of the signal of the reference species. In this case, it is naturally the right portion of the signal modelized from the reference species that will be substituted for the right part of the spectrum of the FID, with the left part carrying the species to be characterized being preserved. For example, it will then be necessary to process the spectrum in two stages (in one case the DFR is kept, and the process is then repeated while keeping the UFR). The species of the UFR may also not appear at the same distance from the reference signal as the species of the DFR and the symmetrisation may also create no problem in this case.

The following description of the invention relates to the consequences of DFRR processing 1320 on noise. The problem of "sidebands" is dealt with afterwards.

As for noise, it is well known that the FFT of a noise signal n(t) having a Gaussian distribution with a zero mean with standard deviation a is a noise signal such that:

$$N(\omega) = \sum_{i=1}^{Npts} n(t) e^{j\omega t/N}$$

which is characterized by a Gaussian distribution with a zero mean and a standard deviation $\sigma\sqrt{N}$ because noises are added in a quadratic way. N is the number of points in time. As the distribution of the noise signal is centred around zero, the modelized signal introduces no discontinuity during the DFRR processing which is naturally a zero signal. The noise obtained in the NMR is characterized by a Gaussian distribution centred on zero. In the absence of a signal, as is the case here, the noise is thus centred on the X axis. In the presence of a signal, the noise is naturally superimposed on the signal, and the return to the centred position then depends on the width of the line of the signal (typically a few Hertz to the half-way width, but in the case of a Lorentzian line, the wings are relatively large) and if the signal is strong (water) this may reach several hundred Hertz.

The DFRR processing 1320 then consists in replacing the DFR N(σ) by zeros which leads to obtain a new signal $\tilde{N}(\omega)$. Without any processing the iFFT of N(ω) naturally leads to the production of the original noise signal:

$$n(t) = \frac{1}{N} \sum_{i=1}^{N} N(\omega) e^{-i\pi\omega t/N}$$

with its standard deviation σ. But, as half the points of N(ω) have been replaced by zeros then the iFFT $\tilde{N}(\omega)$ leads to a new noise signal:

$$\tilde{n}(t) = \frac{1}{N} \sum_{i=1}^{N} \tilde{N}(\omega) e^{-i\pi\omega t/N}$$

$$= \frac{1}{N} \sum_{i=1}^{N/2} \tilde{N}(\omega) e^{i\pi\omega t/N}$$

As half the points have a zero value, the sum can be performed on the other half. The standard deviation σ of ñ(t) is then equal to $$\frac{\sigma}{\sqrt{2}}.$$

It can thus be said, and this is a first result, that the standard deviation of the noise signal ñ(t) obtained during the DFRR processing is reduced by a factor $\sqrt{2}$ when compared to the standard deviation of the original noise signal n(t).

Data processing continues using the module of the signal as described in FIGS. 1 to 9 to obtain a new signal as follows:

$$\tilde{N}_{Mod}(\omega) = FFT(\|\tilde{n}(t)\|)$$

As explained above the module of a noise characterized by a Gaussian distribution with a zero centred mean is distributed according to the so-called Rice law. This distribution can be approximated by a Gaussian distribution when the SNR is above 3, and by Rayleigh's distribution when the SNR tends toward zero. The characteristics of the SNR obtained under both above conditions have already been discussed in the description of FIGS. 1 through 9. The modification introduced by the DFRR processing 1320 only is discussed further. As for the Gaussian distribution, it has been shown that if σ is the standard deviation of n(t) then that of $$\tilde{N}_{Mod}(\omega) = FFT(\|\tilde{n}(t)\|)$$

is equal to σ too. By applying this to the composite spectrum obtained as explained above, the standard deviation of Ñ(ω) is equal to that of ñ(t), which is itself equal to $$\frac{\sigma}{\sqrt{2}}.$$

If the Gaussian approximation is valid the standard deviation of the noise signal obtained using the DFRR transformation is reduced by a factor $\sqrt{2}$ compared to the standard deviation obtained when using the processing of the module only. The decrease in the SNR is observed when the processing with the module is compared with the conventional processing for the same Gaussian approximation of the noise. The DFRR processing makes it possible to recover the lost SNR resulting from the processing of the module in the presence of Gaussian distribution of noise.

As for the above so-called Rayleigh's condition, while noise is no longer centred, the analysis is more complex. The noise characteristics obtained under this approximation are discussed later.

In the following a mathematical representation of the DFRR processing 1320 on these two noise distribution approximations is introduced. These mathematical representations are then used to calculate all the signals used for the simulations. Rayleigh's approximation is first modelized. If r(t) is a noise signal in the time domain, and R(ω) its Fourier transform, replacing the DFR of R(ω) with zeros is exactly equivalent to a multiplication of R(ω) by the inverse of the unit-step function defined as follows:

$$\sqcup\!\!\Gamma(\omega) = 0 \text{ if } \omega > 0$$
$$= 1 \text{ if } \omega < 0$$

The DFRR processing can be summed up as:

$$\tilde{R}(\omega) = R(\omega) \times \sqcup\!\!\Gamma(\omega)$$

and the inverse transform iFFT gives:

$$\tilde{r}(t) \text{FFT}^{-1}(R(\omega) \times \sqcup\!\!\Gamma(\omega))$$

if the module is extracted the following is obtained:

$$\|\tilde{r}(t)\| = \sqrt{\|\text{FFT}^{-1}(R(\omega) \times \sqcup\!\!\Gamma(\omega))\|}$$

and the fast Fourier transform leads to:

$$\tilde{R}_{Mod}(\omega) = FFT(\|\tilde{r}(t)\|)$$
$$= FFT\left(\sqrt{\| FFT^{-1}(R(\omega) \times \sqcup\!\!\Gamma(\omega))\|}\right)$$
$$= FFT\left(\sqrt{\| FFT^{-1}(R\omega)) \otimes FFT^{-1}(\sqcup\!\!\Gamma(\omega))\|}\right)$$
$$= FFT\left(\sqrt{\| r(t) \otimes FFT^{-1}(\sqcup\!\!\Gamma(\omega))\|}\right)$$

The Gaussian approximation can be modelized by adding to the original noise spectrum r(t) a constant signal c(t) defined by:

$$c(t) = c, \forall t$$

This gives a new noise signal:

$$g(t) = r(t) + c$$

Using the same notation as above the following is obtained $$\tilde{G}_{Mod}(\omega) = FFT\left(\sqrt{\| g(t) \otimes FFT^{-1}(\sqcup\!\!\Gamma(\omega))\|}\right)$$
$$= FFT\left(\sqrt{\| (r(t) + c) \otimes FFT^{-1}(\sqcup\!\!\Gamma(\omega))\|}\right)$$
$$= FFT\left(\sqrt{\| r(t) \otimes FFT^{-1}(\sqcup\!\!\Gamma(\omega)) + c \otimes FFT^{-1}(\sqcup\!\!\Gamma(\omega))\|}\right)$$
$$= FFT\left(\sqrt{\| r(t) \otimes FFT^{-1}(\sqcup\!\!\Gamma(\omega)) + c\|}\right)$$

Although $$\tilde{G}_{Mod}(\omega)$$

is much like $$\tilde{R}_{Mod}(\omega)$$

it will be seen hereafter, in the results section, that the shape of the resulting noise is much different.

As for the "sidebands" i.e. the antisymmetric artefacts around the water signal, it has been seen that the symmetrisation induced when processing the module was a simple and effective way to eliminate these from the final spectrum. When substituting the DFR of the spectrum with a model of water, the "sidebands" located in this region are removed and the automatic cancellation induced by the processing of the module is no longer done. A solution for going on eliminating the distortions caused by the "sidebands" in the UFR spectrum is as follows:

$$-\underset{Mod}{S}(\omega)$$

is the spectrum obtained when using the module processing only;

$$-\underset{Mod}{\tilde{S}}(\omega)$$

is the spectrum obtained when using both the module and the DFRR processing;

$$-\underset{Mod}{S}(\omega)$$

does not contain artefacts of the "sidebands" type, whereas $$\underset{Mod}{\tilde{S}}(\omega)$$

still contains some in the UFR part since they have not been cancelled by symmetrisation;

The UFR of the subtraction result $$\underset{Mod}{\tilde{S}}(\omega)$$

minus $$\underset{Mod}{S}(\omega)$$

contains only the "sidebands" and some noise. Such "sidebands" can then be removed, which leads to a spectrum with no contamination by the antisymmetric artefacts of the "sidebands" type. The process representing this transformation and how it is introduced into the DFRR processing 1320 appears in the box 1350 of FIG. 13.

In this figure, the step 1351 corresponds to the subtraction of the spectrum $$\underset{Mod}{S}(\omega)$$

from the spectrum $$\underset{Mod}{\tilde{S}}(\omega)$$

to octan the "sidebands" 1352. The step 1353 corresponds to the subtraction of the "sidebands" 1352 from the spectrum $$\underset{Mod}{\tilde{S}}(\omega)$$

to obtain a new spectrum 1354 wherein the "sidebands" 1352 are removed.

Figure 12C:
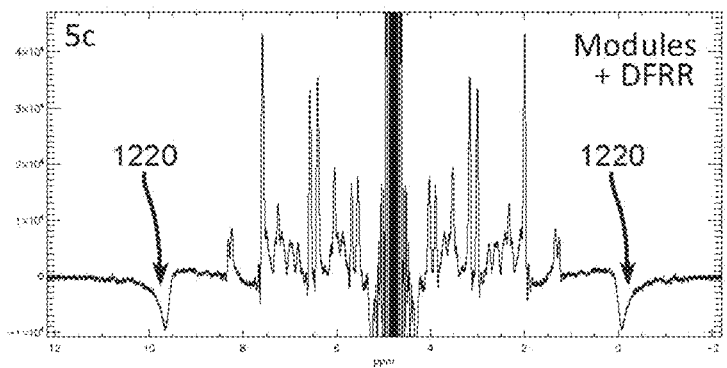
Figure 12D:
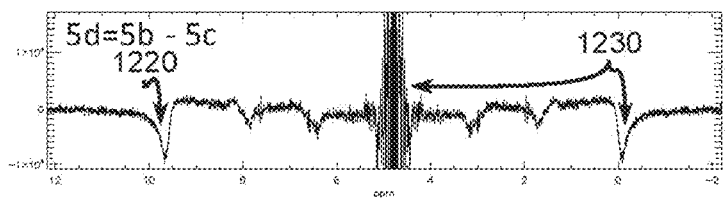
Figure 12E:
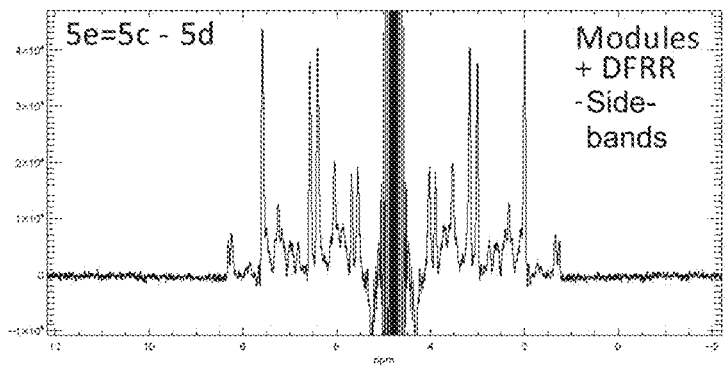

It should be noted here that the subtraction 1351 can be carried out either on the FID, as shown in FIG. 13 or on the spectrum as shown in FIG. 12c-12e, with the FFT being distributive with respect to the addition.

Preferably but optionally, a smoothing function is applied to the subtraction obtained.

This embodiment has the particular advantage of being particularly simple, reliable and effective to improve the SNR. It thus makes it possible to take advantage of the benefits of the module by automatically removing the anti-symmetric artefacts but without the limitations usually induced by the module with the superposition of the noise present on either side of the resonance frequency of the reference species.

The case of CSI-type experiments, i.e. when analyzing several voxels is examined hereunder. As indicated above, the reduction by a factor $\sqrt{2}$ of the SNR has never been observed in practice in the in vivo experiments carried out when implementing the method based on the taking into account of the module. Within the scope of the present invention, it has been identified that this is due to the fact that most of the examples were extracted from CSI type experiments and to the way the processing module has been implemented by the process shown in box 1310 of FIG. 13. As already seen, an FFT 1311 is first executed in the spatial dimension, and followed by a calculation of the module 1314 of each voxel of the CSI. This makes it possible to correct any phase and frequency shift in the spatial domain. Then, an inverse transform iFFT 1317 is performed in the spatial dimension which makes it possible to obtain a new set of data of the k space. Then, the conventional processing is performed 1360. During this conventional processing a spatial filtering is carried out.

Spatial filtering is applicable as soon as CSI are involved, whether they are acquired by one or more coil(s) or not.

Spatial filtering can be applied:
  either before the taking into account of the module, in the case where the steps 1321 to 1326 are executed or in the case where such steps 1321 to 1326 are not executed.
  or, after taking account of the module, in the case where the steps 1321 to 1326 are executed or in the case where such steps 1321 to 1326 are not executed. An increase in the signal to noise ratio which is added to the one provided by the steps 1321 to 1326 if they are executed.

The spatial filtering is preferably performed by multiplying the CSi by a bell (e.g. Gaussian, cosine, Hanning, Hamming, . . . ) function in the dimension of the spatial encoding (thus in the k space), before the spatial Fourier transform.

One consequence of the spatial filtering is a reduction in the spatial resolution, i.e. an increase in the size of the voxels. This means that, after the spatial filtering, the new spectrum is the result of the sum of the original spectrum and a part of the spectrum surrounding the original spectrum. If the spatial filtering is performed after processing the module, the spectra of the CSI are aligned together in phase and frequency. This means that whatever the new voxel size obtained after filtering, all voxels involved are aligned together in phase and frequency. This further means that there is no increase in the width of the lines due to the increase in the size of the voxels. On the contrary, if spatial filtering is performed prior to extracting the module, the voxels involved are not aligned in phase and frequency and the resolution of the resulting spectrum can be degraded leading to a decrease in the SNR, as illustrated in the following section giving the results.

Figure 22:
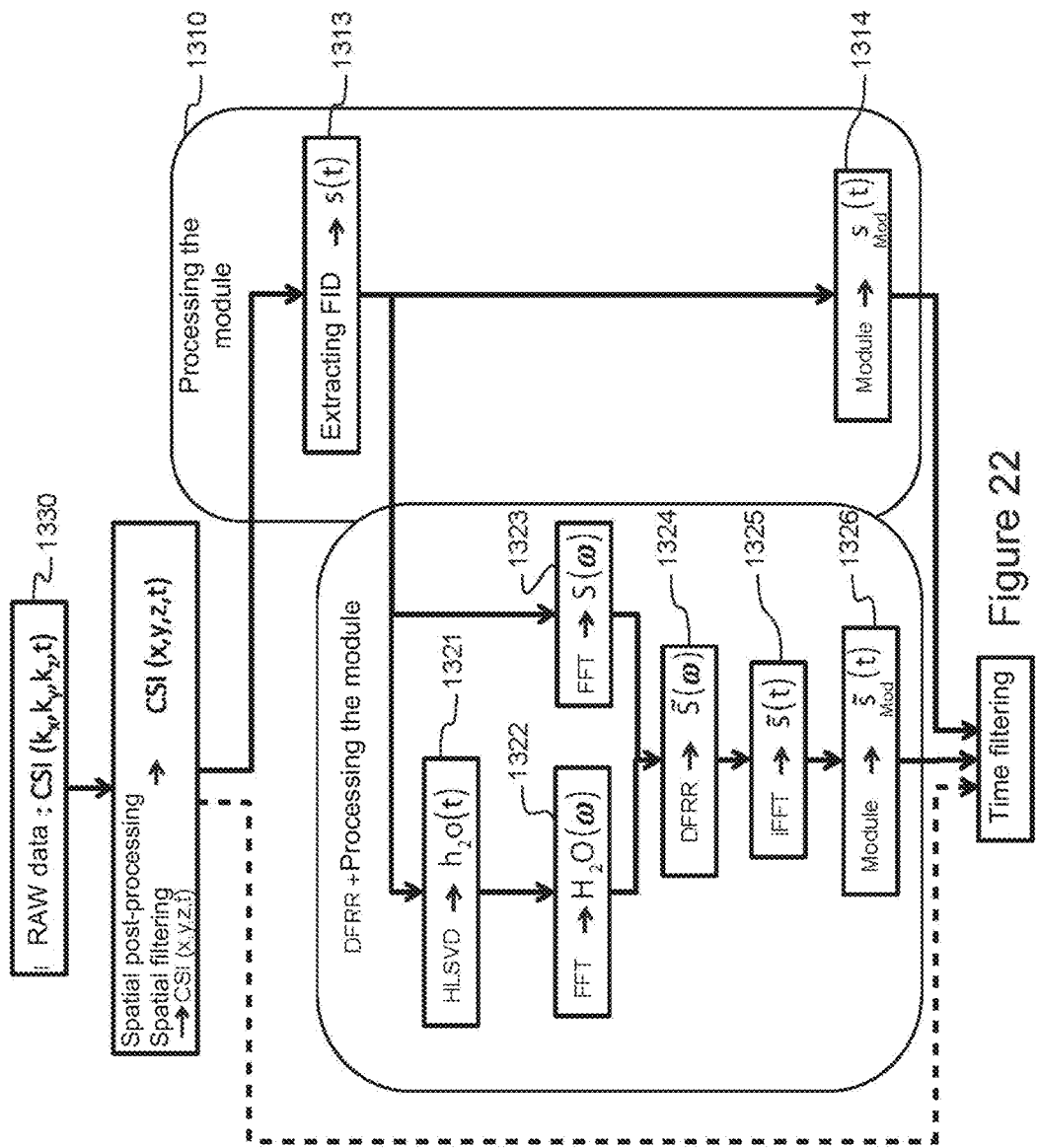
FIG. 22 is a flow chart of the steps of one embodiment of the method according to the invention.

FIG. 22 is partly the same as FIG. 13. The steps having the same references as those in FIG. 13 are identical to those described above while referring to FIG. 13. This figure illustrates in dotted lines the conventional processing (without taking the module into account). It also illustrates the processing 1310 by the module applied to the complex FID signal S(t) (step 1314). This flow chart also illustrates the DFRR processing combined with the processing by the module (steps 1321 to 1326). In the latter two processings, spatial filtering is performed prior to calculating the module (steps 1314 or 1326) with the consequences discussed above. The case where the spatial filtering is performed after the steps 1314 or 1326 will thus be preferred.

In this figure, the processing of the sidebands, which is an optional optimization of the invention, is not shown.

In the case of a single-voxel analysis, processing is greatly simplified since the whole spatial processing disappears. The steps 1131, 1312 and 1317 of FIG. 13 are no longer needed and the step 1313 becomes extracting a FID among those that have been acquired. In step 1326, we have a FID that can be quantified in the time domain, or a temporal Fourier transform can be performed to obtain a spectrum that can be quantified in the spectral domain. Whatever the method chosen, the final validation of the result will preferably be in the spectral domain since this is a space where an operator can easily judge the quality of a spectrum. As a matter of fact, SNR, presence or absence of artefacts, width of lines cannot be visually assessed by an operator in the time domain.

When the experiment is repeated several times to improve the SNR, the processing will be executed for each FID before summing same (step 1315) of FIG. 13. The steps between 1313 and 1315 of FIG. 13 may replace the steps 340 of FIG. 3, with the step of "Calculation of the Module of each FID" in FIG. 5 (in the case where the module is calculated after the spatial filtering) and the step 340 of FIG. 8, as is apparent from the foregoing description.

In this paragraph, the experimental framework for in vivo and in vitro applications of the invention is more particularly described. The assumptions used for the implementation of the invention were first tested on simulations and then in experiments. In vivo experiments were conducted from NMR equipment of the "scanner" type which can develop a field with a value of 3 tesla (Verio, Siemens Medical Solutions, Erlanger, Germany) using a so-called OVS-CSI specific pulse sequence. Most spectra presented in the results section below are excerpts from CSI experiments obtained with 25×25 encoding pitch, a circular type of weighting, and a short echo time, or "25×25 circular weighted short echo time" with or without low water suppression. Acquisition parameters are: TR/TE=1,500/16 ms, sampling points=2,000, SW=2,000 Hz. The field of vision is 240×240 millimeters (mm) and the wafer is 20 mm thick. The total acquisition time is 11 minutes and 7 seconds. The results of CSI experiments with long echo times are also presented in particular with an echo time of 135 ms, with all the other parameters remaining the same. The subsequent processing was carried out using so-called CSIAPO specific software which applies a so-called Hanning spatial filtering, a zero padding of the acquired data on 8,000 sample points in the time domain and removing the residual water signal using the HLSVD technique. All spectra obtained with the processing of only one module or with the processing of a module plus DFRR are multiplied by a factor of two to compensate for the reduction in the strength of the signal by the same factor induced by the processing of the module. These spectra are then easier to visually, as compared with the spectra obtained with the conventional processing of the signals.

In the following description of the invention, the results of the simulations carried out to verify the assumptions of implementation of the invention are described.

In order to visualize the shape of the noise signal obtained, respectively, with Rayleigh's distribution and the Gaussian approximation, two complex noise signals have been generated using so-called "IDL" software developed by the "Interactive Data Language, Research Systems Inc." company located in Boulder, Colo., USA. The first signal r(t) 1411 consists of a normal distribution, in the statistical meaning of the word, composed of twice 4,000 samples forming a pseudo-random sequence with a zero mean and a standard deviation of 10 and representing Rayleigh's distribution. The second signal g(t) 1412 is obtained by adding a constant signal with amplitude of 50. It represents the Gaussian distribution.

Figure 14:
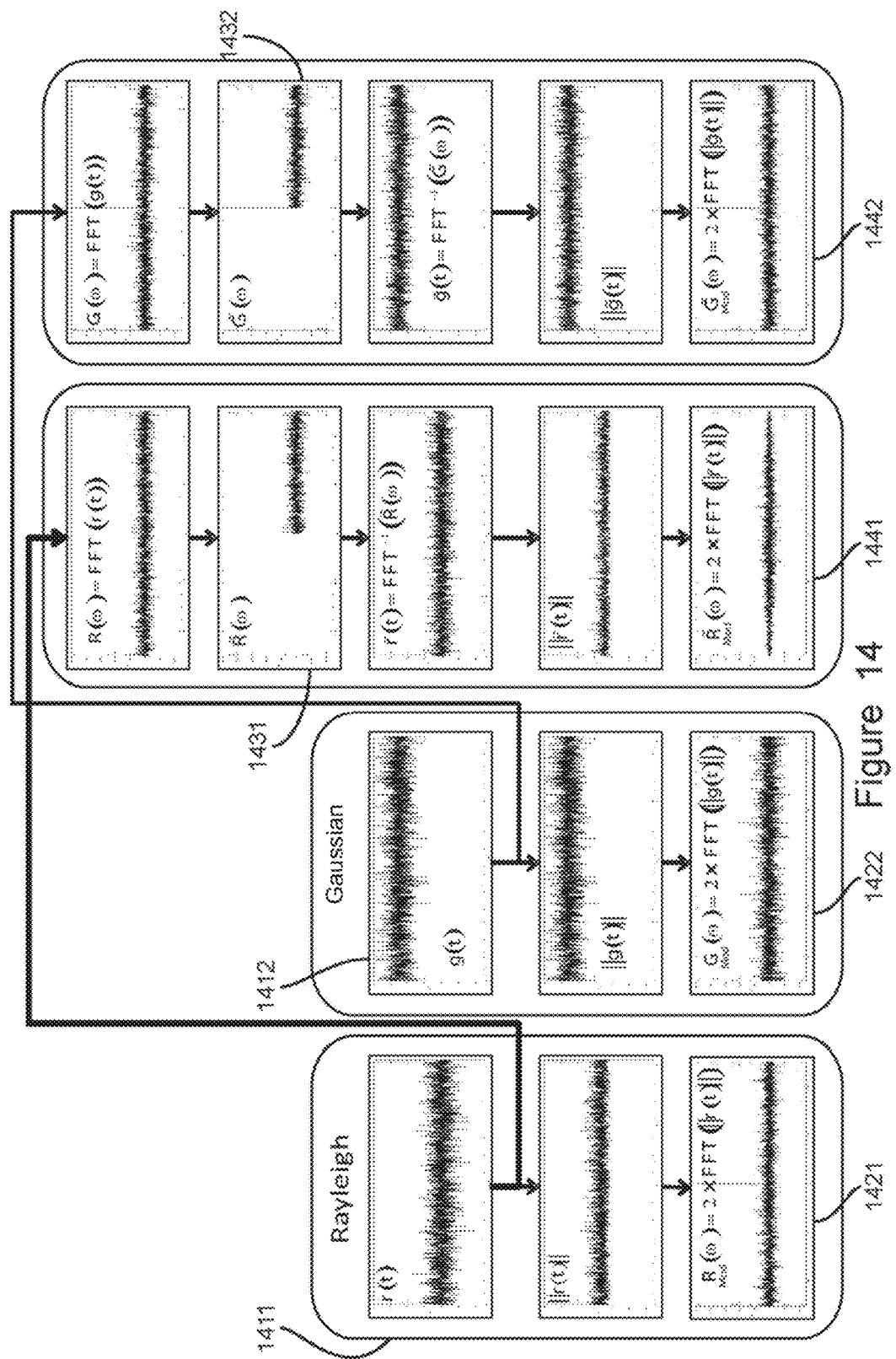
FIG. 14 illustrates the noise simulation results obtained with different implementations of the method of the invention.

FIG. 14 shows the results obtained on these two noise signals during each step of the processing using either the processing of the module only or the processing of the module with DFRR. For processing the module, both modules ‖r(t)‖ and ‖g(t)‖ are extracted and after the transform FFT, the noise spectra $$\underset{Mod}{R}(\omega) \text{ and } \underset{Mod}{G}(\omega)$$

are obtained. As already discussed, these noise signals are multiplied by a factor of two to compensate for the loss of amplitude of the signal induced by the processing of the module. The modification of the SNR can then be visually estimated by the single evaluation of the noise amplitude. As regards the processing DFRR, a Fourier transform is applied to the signals r(t) and g(t), which respectively leads to obtaining the signals $$\underset{Mod}{R}(\omega) \text{ 1421 and } \underset{Mod}{G}(\omega) \text{ 1422,}$$

i.e. the noise signals which would be obtained with the conventional processing. The DFR of each signal is then replaced by zeros, an operation upon completion of which $\tilde{R}(\omega)$ 1431 and $\tilde{G}(\omega)$ 1432 are obtained. Then, an inverse Fourier transform or iFFT is applied to these two signals, the module is extracted and a FFT is applied again and multiplied by a factor of two for the same reason as above, which leads to the final result $$\underset{Mod}{\tilde{R}}(\omega) \text{ 1441 and } \underset{Mod}{\tilde{G}}(\omega) \text{ 1442.}$$

If more particularly the signal $$\underset{Mod}{\tilde{R}}(\omega) \text{ 1441}$$

is more particularly considered, it is clear that the DFRR processing leads to obtaining a non-uniform noise in the spectral dimension. It should be reminded that Rayleigh's condition is the one that gives no degradation of the SNR when using the processing of one module $$\left(\underset{Mod}{R}(\omega)\right),$$

which should be compared to the conventional processing (R(ω)). When the DFRR processing is added to $$\left(\underset{Mod}{R}(\omega)\right)$$

the noise around the centre of the spectral window has substantially the same intensity as the one obtained using the processing of one module, whereas a reduction in the noise intensity can be observed when moving toward the edges of the spectral window.

If attention is more particularly paid to the signal $$\underset{Mod}{\tilde{G}}(\omega),$$

it is clear that the amplitude of the noise is reduced as compared to $$\underset{Mod}{G}(\omega).$$

It is comparable to the one of G(ω) which is the noise obtained when the conventional processing is used.

Tables 1a and 1b hereunder show the standard deviation of the noise obtained at different interesting steps, when such simulation is repeated 1,000 times. Table 1a shows the results obtained in the time domain and Table 1b in the frequency domain. Again, the signals obtained after processing the module, with or without DFRR processing, are multiplied by a factor two to compensate for the loss of signal strength created by this processing. The standard deviation of the noise is directly related to the SNR.

| 1a | r(t), g(t) | r̃(t), g̃(t) |
|---|---|---|
| Standard deviation | σ | $\dfrac{\sigma}{\sqrt{2}}$ |
| Measured (calculatrf) | 10.0 (10.0) | 7.07 (7.07) |

| 1b | R(ω), G(ω) | $R_{Mod}(\omega) \times 2$ | $G_{Mod}(\omega) \times 2$ | $\tilde{R}_{Mod}(\omega) \times 2$ (centre) | $\tilde{R}_{Mod}(\omega) \times 2$ (bord) | $\tilde{G}_{Mod}(\omega) \times 2$ |
|---|---|---|---|---|---|---|
| Standard deviation | $\sigma\sqrt{N}$ | $\sigma\sqrt{2N}$ | $\sigma\sqrt{N(4-\pi)}$ | ? | ? | $\sigma\sqrt{N}$ |
| Measured (calculated) | 640.5 (640) | 895.0 (905.1) | 593.0 (592.6) | 576.1 | 138.3 | 637.3 (640) |

This table shows that, in the areas where the noise of the original FID signal follows a Gaussian distribution, i.e. with a standard deviation that tends toward zero, the SNR of the spectra obtained using the processing of the module with DFRR is increasing by a factor $\sqrt{2}$, when compared to the SNR of the spectra obtained using the processing of a single module. The SNR obtained using the module with DFRR is then the same as the one obtained using the conventional processing. In the region where the noise of the original FID signal obeys Rayleigh's law, i.e. when the SNR of the FID is above 3, the SNR of the spectra obtained using the processing of the module with DFRR is even higher than the one obtained using the conventional processing. This gain can reach a factor of 4.6 near the limits of the spectral window. In practice, both regions are present in an acquired FID signal and the resulting SNR is between these two limits depending on the relationship existing between the noise that can be approximated by a Gaussian distribution and the one which approaches Rayleigh's distribution in the original FID signal.

If, for various reasons, the condition required for Rayleigh's law to apply is not desirable, it should be noted that it is possible to add a constant signal just prior to extracting the module and to remove it after extracting the latter. If the value of the constant signal is chosen to be greater than three times the standard deviation of the noise of the original FID signal, the condition for considering that the distribution is a Gaussian one is then satisfied. The SNR of the spectra obtained using the processing of the module with DFRR shall be the same as the one of the spectrum obtained using the conventional processing. The gain in SNR will be lost but the noise of the resulting spectrum will then be flat. The frame 1370 of FIG. 13 shows how this additional processing can be introduced into the processing of the DFRR 1320.

All the hypotheses enabling the implementation of the invention have also been tested in vivo and in vitro as described in the next section. The results with the DFRR processing, the processing of a single module and the conventional processing have been compared. In vivo NMR spectroscopic/spectrometric data of the brain and in vitro ones of a "phantom" have been obtained using the experimental conditions described above.

As is known, a phantom is a model of what shall be studied. For example, it may be a water-containing vessel and a few metabolites that are found in the brain.

Figure 15:
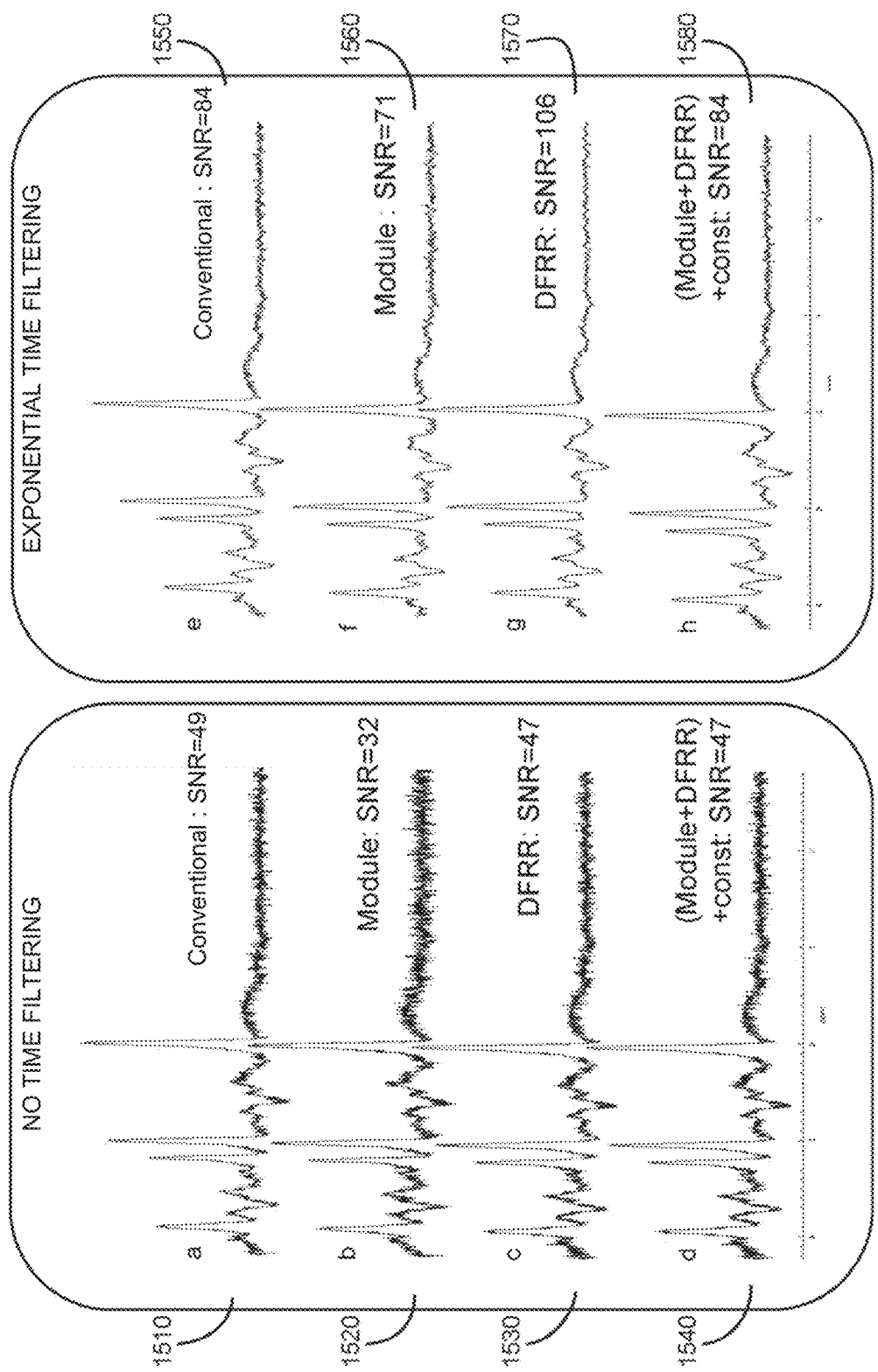
FIG. 15 shows spectra extracted from the same voxel of a long echo CSI acquisition on a brain without water suppression.

FIG. 15 shows eight spectra extracted from the same voxel of a long echo CSI acquisition on a brain without water suppression. Graphs 1510, 1520, 1530 and 1540 each represent a spectrum obtained with, respectively, the conventional processing, the module processing, the module processing with DFR and with addition of a constant signal. This is done without apodization in the time domain in order to maximize the Gaussian noise contribution. This actually consists in multiplying the FID by a decreasing exponential which favours the beginning of the FID (i.e. the area where there is a signal) and attenuates the end of the FID (where only noise remains). The graphs 1550, 1560, 1570 and 1580 show the spectra obtained using the same processings but adding an exponential temporal filtering with a bandwidth of 0.5 so as to favour the conditions for obtaining Rayleigh's distribution.

The SNRs obtained using the various processing techniques are shown in FIG. 15 and it can be verified that, when the Gaussian condition is favoured 1520, 1530 and 1580, the SNR obtained using the conventional processing is recovered by using the DFRR processing.

It can also be verified in this example that adding a constant to the FID signal before extracting the module and the removing thereof from the FID signal in areas where Rayleigh's law applies 1580, leads to reducing the SNR of the resulting spectrum as compared with the spectra obtained when Rayleigh's condition is favoured 1570. The SNR of the resulting spectrum is then the same as the one obtained using the conventional processing. It should also be noted that a decrease in SNR by a factor $\sqrt{2}$ is actually obtained when comparing the conventional processing 1510 with the processing of the module 1520. This is due, in such particular cases, to the fact that the module and DFRR processing are performed after the spatial filtering in order to eliminate the gain in SNR which can be obtained when they are carried beforehand, as previously discussed (CSI experiments). The results shown have been obtained by example from a CSI obtained with a 25×25 encoding pitch. Such results could be compared to those obtained with a single voxel experimentation. FIG. 15 illustrates what the DFRR processing alone brings. The processing by the module has been performed after the spatial apodization so as not to add the gain in SNR obtained when it is executed beforehand. Therefore, although the results of this figure have been obtained on a CSI, they are equivalent to those which would have been obtained on a single voxel.

Figure 16:
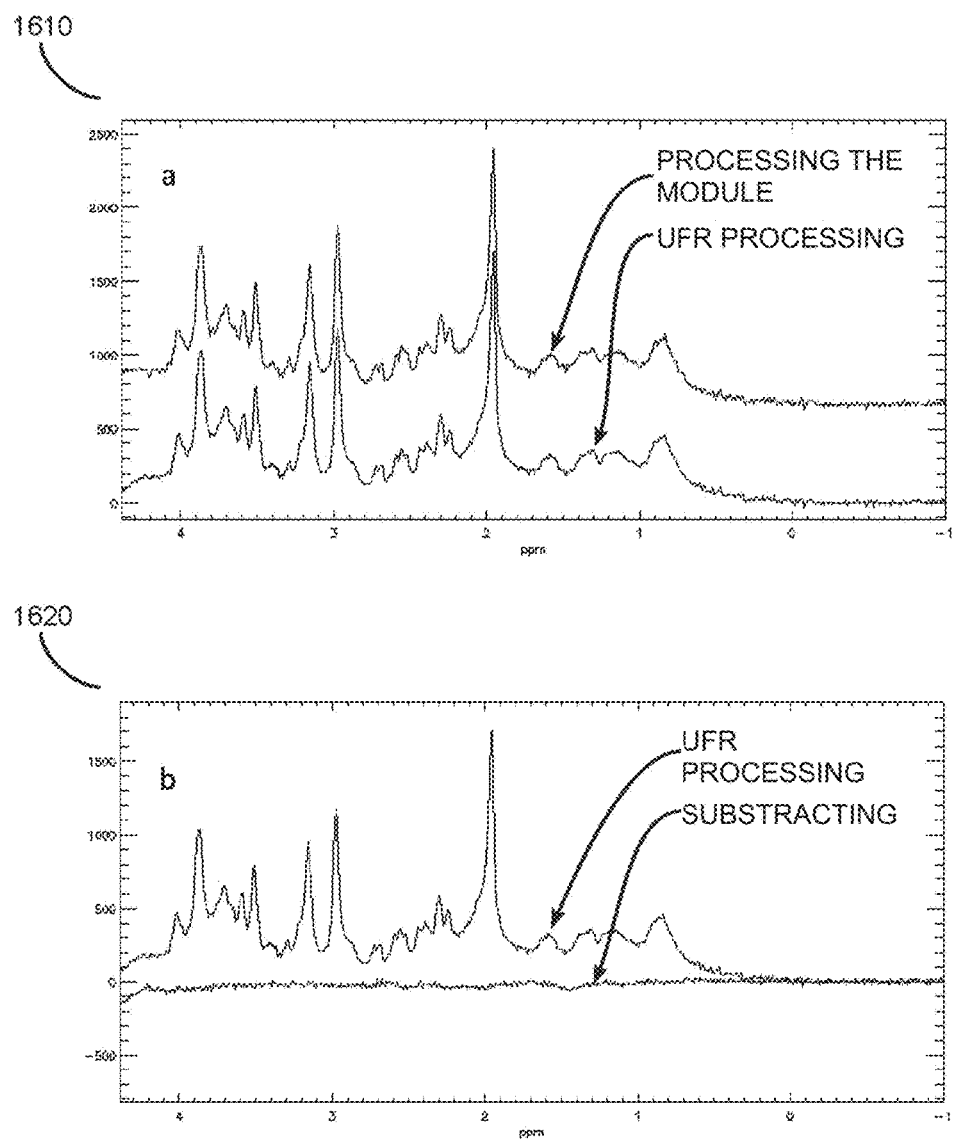
FIG. 16 shows two spectra of the same voxel of a short echo CSI acquisition performed on a brain with a partial suppression of water.

FIG. 16 shows two spectra of the same voxel of a short echo CSI acquisition performed on a brain with only a partial suppression of water in order to minimize the "sidebands". The diagram 1610 shows the spectrum obtained using the processing of one module and the spectrum obtained with the DFRR processing. The diagram 1620 shows the result of the subtraction between the spectrum obtained using the DFRR processing and the processing of the single module. It can be seen in this curve, which is the result of the subtraction, that there is no residual signal from the metabolites. The subtraction signal only consists of noise and artefacts which are probably "sidebands."

Figure 12F:
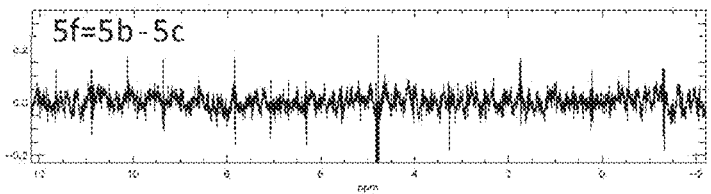

As seen above, antisymmetric artefacts of the "sidebands" type can clearly be identified on FIG. 12a, which corresponds to a short echo CSI acquisition on a phantom which contains several metabolites in order to mimic a brain spectrum. FIGS. 12a and 12b already described and FIG. 12c respectively show the spectra obtained using a conventional processing, processing with the single module and processing of the module plus the DFRR. As already described, the "sidebands" are removed upon processing the single module but not in the case of the processing of the module plus the DFRR, as can be seen 1220. FIG. 12*d* shows the result of the subtraction between the spectra of FIGS. 5*b* and 5*c*, i.e. the difference between one single module and module plus the DFRR. Residual water between 4 and 4.95 ppm 1230 and the sidebands can clearly be found. FIG. 12*e* shows the spectrum obtained when this signal is subtracted from the signal, after processing the module with the DFRR, i.e. the one of FIG. 5*c*. It can be seen on the spectrum of FIG. 12 that the "sidebands" are then actually suppressed, and that this spectrum is very similar to the one obtained using the processing module only, i.e. the one of FIG. 12*b*. FIG. 12*f* shows the result of the subtraction between the spectrum obtained with the processing of one single module and the spectrum obtained after subtracting the "sidebands", using the DFRR method. This spectrum mainly comprises artefacts, if any, of the "sidebands" type. Therefore, this result clearly confirms that the DFRR method is very effective to remove any sidebands.

Figure 17:
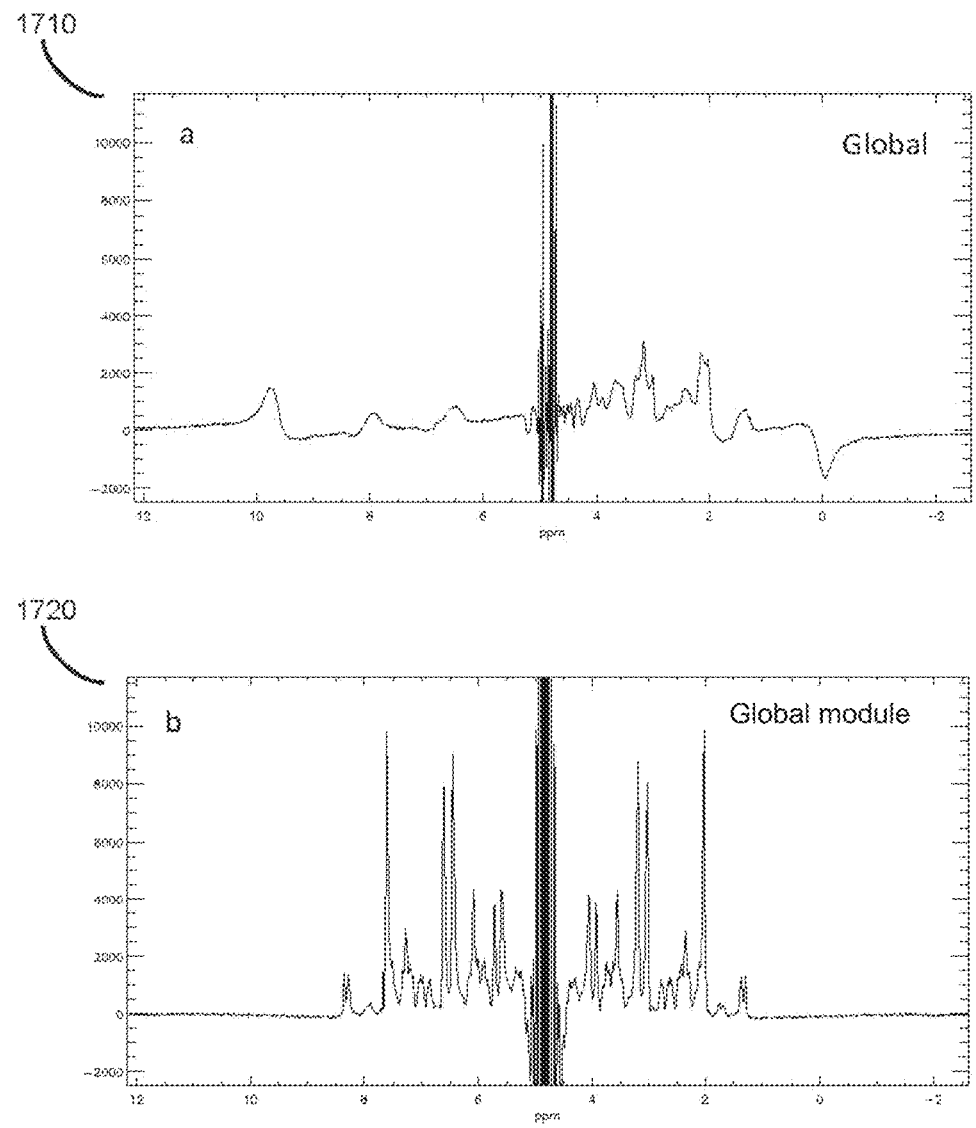
FIG. 17 illustrates the differences which can be achieved when the module is processed before or after the spatial filtering on a short echo CSI acquisition on a phantom.

FIG. 17 illustrates the differences which can be achieved when using the module processing before or after the spatial filtering on a short echo CSI acquisition on a phantom which mimics a brain spectrum. Preferably, the spatial filtering in this case consists in multiplying the rows and columns of the CSI with a Hanning function before the spatial Fourier transform (i.e. in the k space). The diagrams 1710 and 1720 show the global spectrum obtained by summing all the spectra of the CSI. The diagram 1710 shows the spectra obtained using no processing at all, with the resulting spectrum being the spectrum of all the excited portion of the sample, i.e. 2 cm, which corresponds to the wafer thickness selected by the pulse sequence in this case.

As mentioned above, the spatial filtering results in the summing of the spectra of neighbouring voxels. To leverage the phenomenon, this figure sums all the spectra of the CSI. The diagram 1710 shows what is obtained if the spectra are summed before the module is taken into account (which amplifies what would have been obtained if spatial filtering had been performed before the taking account thereof) and 1720 if the module is applied before summing the spectra.

The low frequency resolution that can be noted on this spectrum is due to the difficulty to homogenize the magnetic field over such a large volume. The diagram 1720 shows the spectrum obtained by summing all spectra of the CSI, obtained using the module processing as shown in the box 1310 of FIG. 13.

FIG. 17 further clearly illustrates that the spatial resolution is significantly improved. The module processing in this case acts as if a very high homogeneity of the field B0 had been obtained during the acquisition, whereas this apparent good homogeneity results from the processing. This opens a new perspective in the case where a single voxel must be acquired on a large volume, thus a field difficult to homogenize. As a matter of fact, it may be worth considering acquiring CSI instead, then carrying out the module processing to ultimately obtain a good quality spectrum. Such technique is greatly simplified when taking into account the module as provided by the invention.

Figure 18:
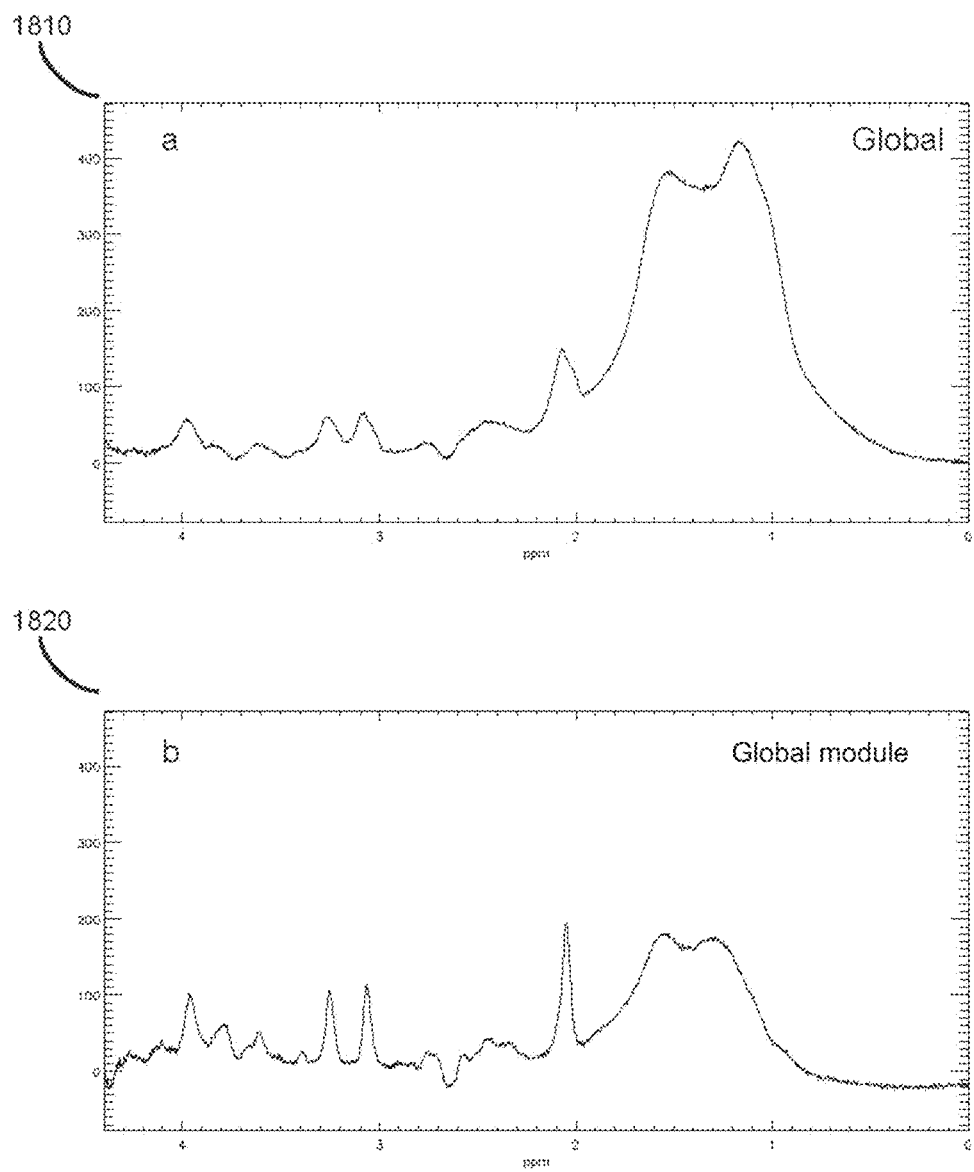
FIG. 18 is the same illustration as the previous figure on a brain.

FIG. 18 shows the results obtained using the same pattern from a long echo CSI acquisition on a brain. A gain in spectral resolution obtained with the module processing, as compared to the spectrum obtained from the raw data, can also be observed. It should also be noted that, in some voxels, the lipid signal may be greater than that of water. In this case, the lipid signal is taken as a reference in the module processing. The spectra of these voxels are then aligned in phase and frequency according to the resonance of such lipids. Fortunately, in the spectroscopy/spectrometry of the brain, such a region contains no interesting resonance. In addition, if the maximum of the resonance of the lipids is about 0.8 ppm, it will be shifted to 4.7 ppm (water resonance position). The water resonance will then be separated into two parts (due to the symmetrisation induced by the taking into account of the module) which will then be positioned, about 8.8 to −0.8 ppm, which thankfully corresponds to a region outside the region of interest. It can be seen from FIG. 18 that the spectrum of interest is between 2 ppm (NAA) and 4 ppm (creatine). The peak located at about 2 ppm corresponds to NAAs and the peak located at about 4 ppm corresponds to creatine. The mass located between 0.8 and 1.8 ppm is that of lipids. However, this effect will act as a subsequent processing for removing the lipids since, in all the voxels wherein the lipid signal is higher than the water signal, the lipid signal will be reallocated to the water resonance and will be removed with the water signal when removing the residual water. This is why the lipid signal is higher on the spectrum obtained without processing the module 1810 which can be compared with the spectrum obtained with the processing of the module 1820.

Figure 19:
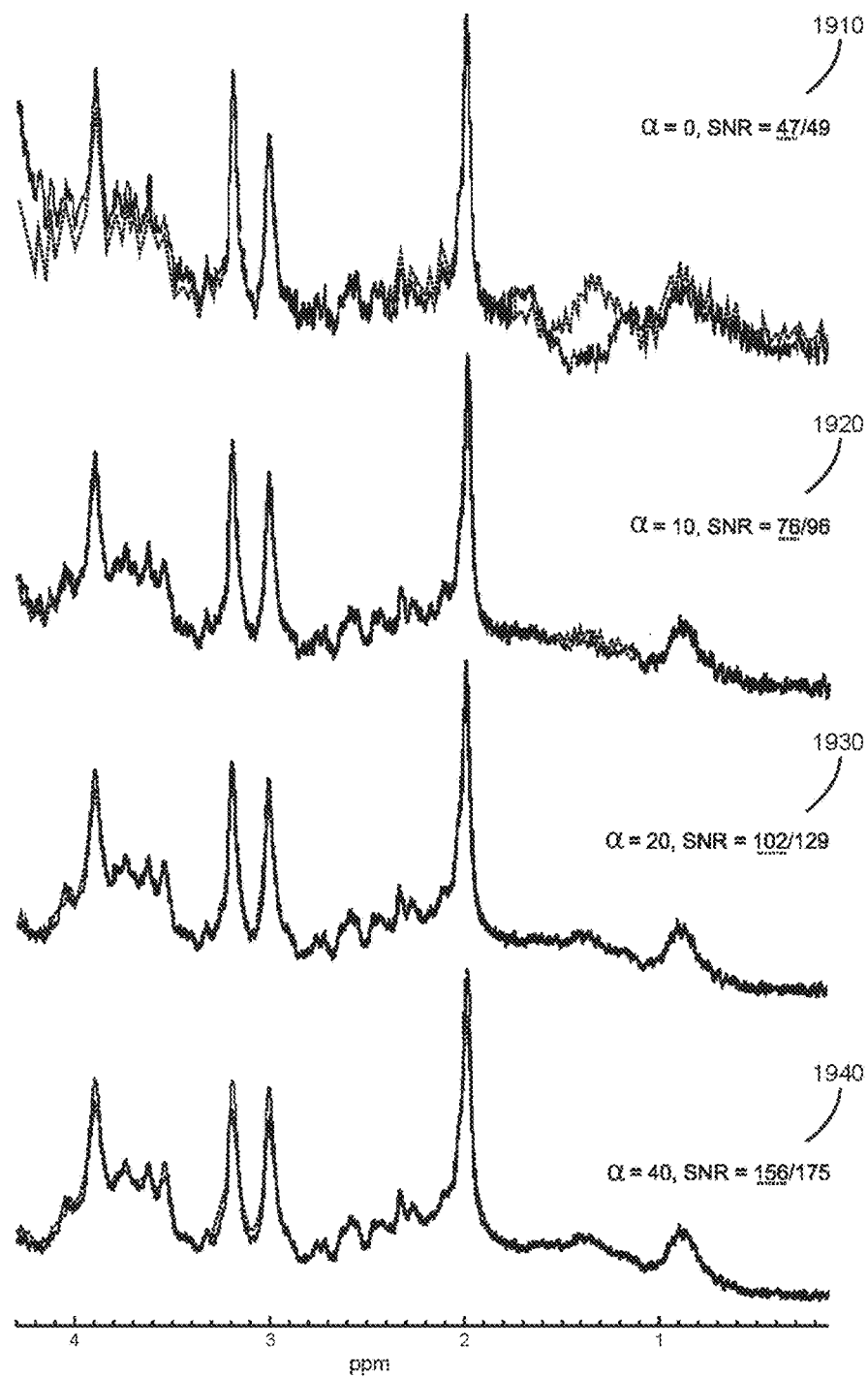
FIG. 19 shows the influence of applying the processing of the module before or after the spatial filtering on a long echo CSI acquisition of a brain.

FIG. 19 shows the influence of the application of the processing with the module before or after the spatial filtering on a long echo CSI acquisition of a brain. In this case, the spatial filtering function is a so-called Kaiser-Bessel window. FIG. 19 shows the spectra obtained when the module is carried out beforehand (dotted lines) and afterwards (solid lines).

The higher $\alpha$ is, the narrower the filter and thus the stronger the filtering. Now, the stronger the filtering, the larger the size of the voxel thus the more the neighbouring voxels, the signal of which is added to the considered voxel.

Furthermore, the signals which are added to the considered voxel come from areas that are increasingly remote from the considered voxel, so from regions wherein the spectrum is most likely to be out of phase and shifted by the inhomogeneity of the magnetic field B0. For $\alpha=0$ there is no spatial filtering, and the SNRs of both spectra are equivalent. For $\alpha>0$, it can be seen that the SNR obtained when the processing by the module is performed before the spatial filtering is better than the one which is obtained when it is carried out afterwards, and that the deviation between both SNRs increases with $\alpha$ (therefore with the voxel size). The above-mentioned feature, which relates to the fact that the expected loss in theoretical SNR due to the processing by the module is not obtained in the case of the CSI, if the spatial filtering is carried out after the extraction of the module, can be noted again here.

Figure 20:
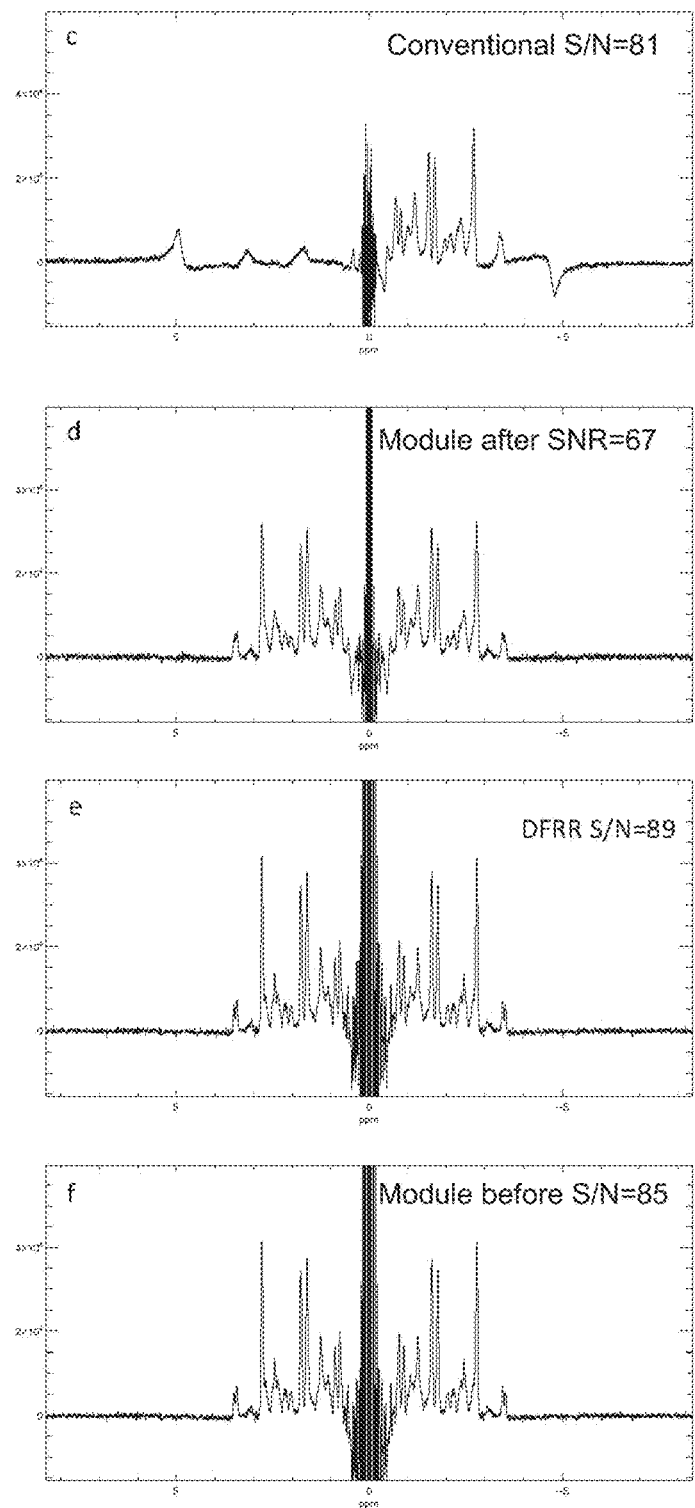
FIGS. 20 and 21 illustrate the same effect as the one of the preceding figure on a CSI acquisition performed firstly on a phantom and, secondly, on a patient.
Figure 21:
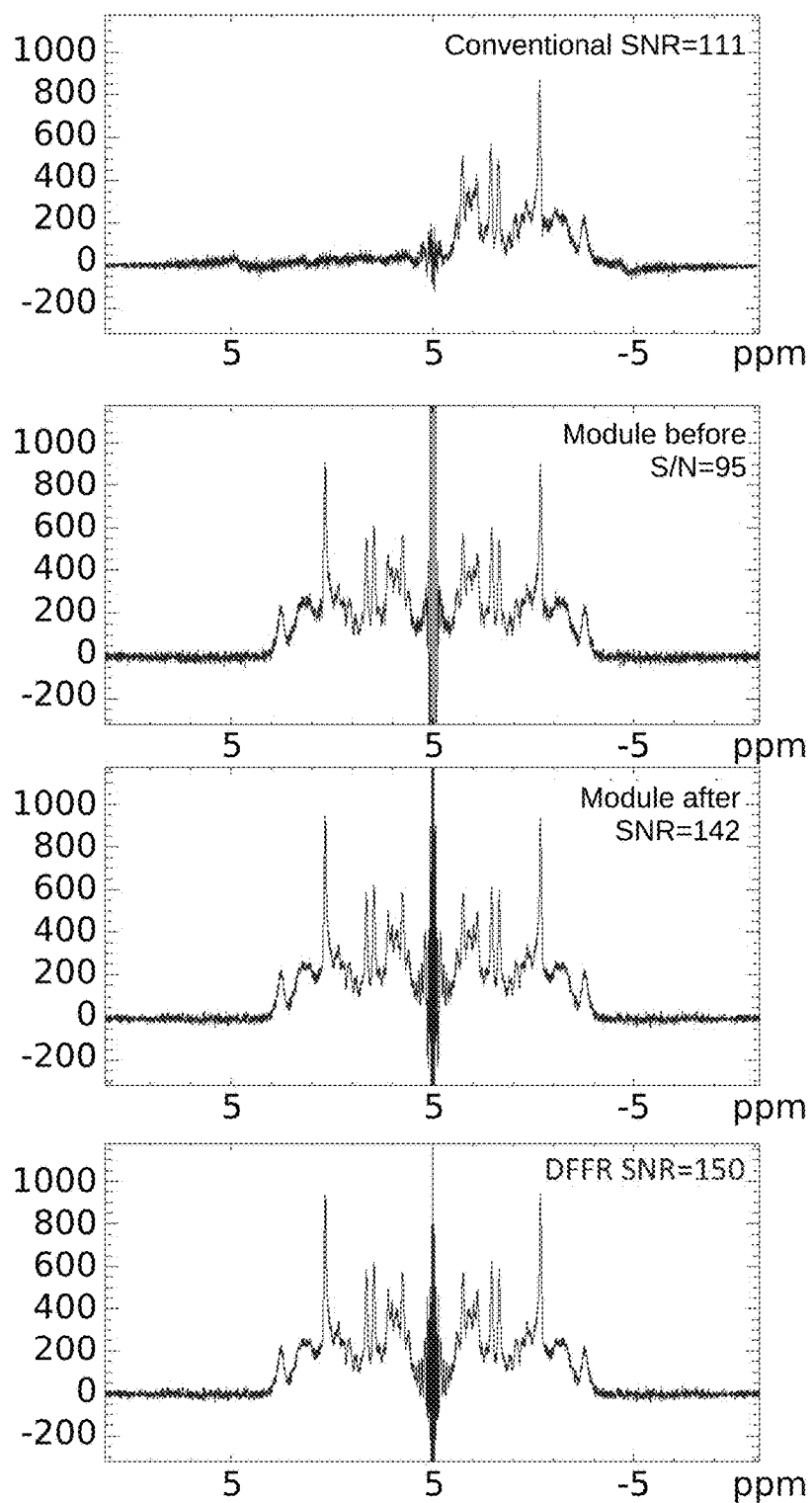

FIGS. 20 and 21 illustrate this effect on a CSI acquisition performed on the one hand on a phantom (FIG. 20) and, on the other hand, on a patient (FIG. 21).

Each of these figures comprises the following spectra illustrated from the top downwards in these figures:
  spectrum obtained using the conventional method,
  spectrum obtained using the module method as described while referring to FIGS. 1 to 9, while taking into account the module after the spatial filtering,
  spectrum obtained using the DFRR method,
  spectrum obtained using the module method as described while referring to FIGS. 1 to 9, taking into account the module before the spatial filtering.

These spectra show that the DFRR technique and the technique of using the module before the spatial filtering make it possible to obtain very satisfactory even improved SNRs as compared to the conventional method. This gain in SNR is even more evident in FIG. 21. This is probably due to the magnetic field inhomogeneities which are higher on a control than on a phantom.

Figure 23:
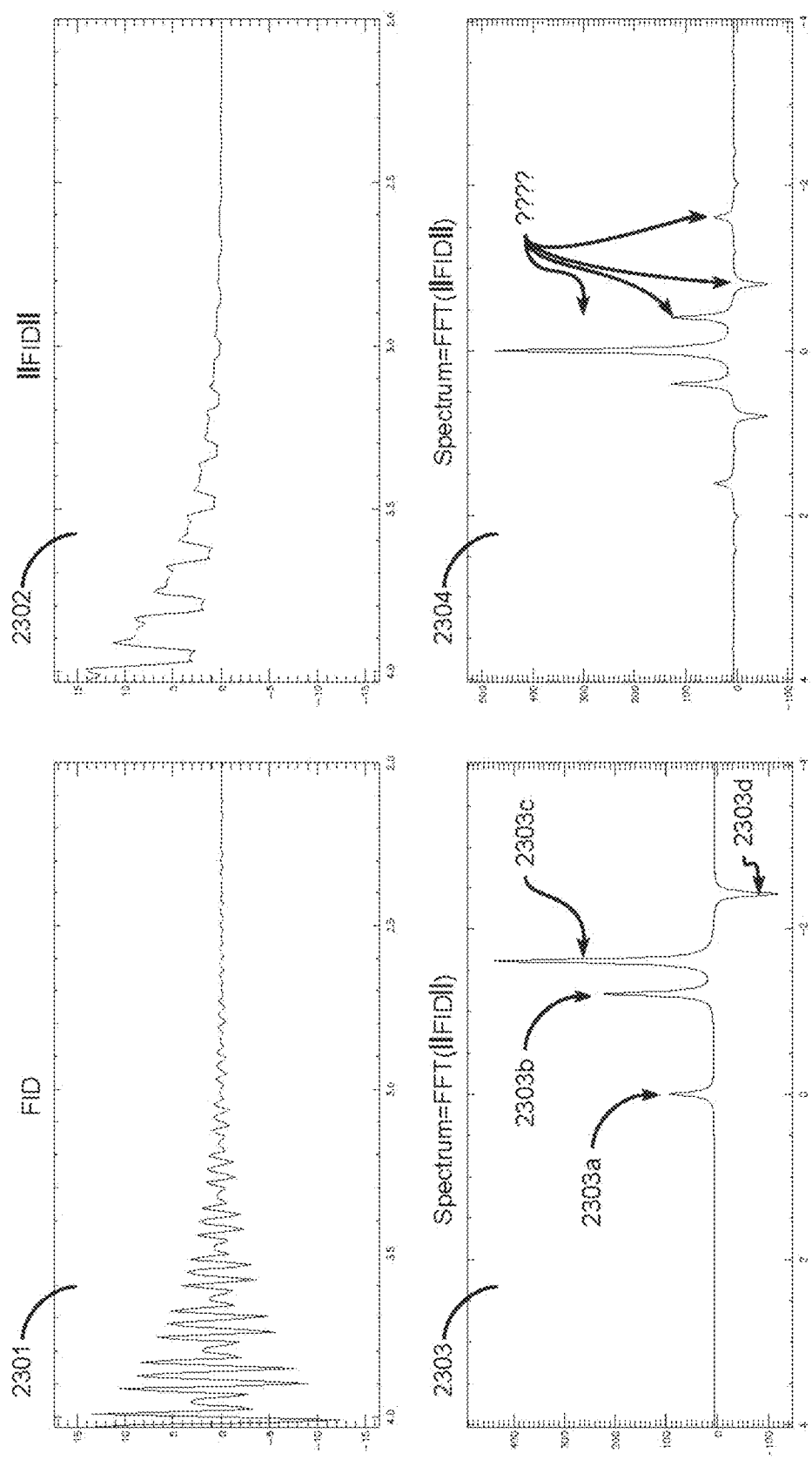
FIG. 23 illustrates the need to preserve at least a part of the reference signal during the acquisition in order to efficiently implement the method of the invention.

FIG. 23 clearly shows that, when the sample comprises several species to be characterized, the invention requires the presence of a reference species in large quantities in order to be used as a carrier for the species to be characterized. As a matter of fact, taking into account the module affects the carrier while enabling to compare the latter with the signals of the species to be characterized.

The invention is thus clearly different from techniques which aim at analyzing the relaxation time of a single species and for which the frequency of the magnetic field is adjusted.

The invention particularly applies to spectroscopy/spectrometry whether single-voxel or multi-voxel (CSI).

Removing the water signal during the acquisition, then applying the module to the signal obtained would make any quantification of metabolites impossible. This clearly appears in FIG. 23 which relates to a spectroscopy/spectrometry. The FID 2301 is obtained after the almost complete suppression of the water signal, with such suppression being carried out during the acquisition. The FID 2302 is obtained after the almost complete suppression of the water signal and after taking into account the module. The spectrum 2303 is the spectrum obtained using a Fourier transform of the FID 2301 and a manual phase correction. On the spectrum 2303, the metabolites can be identified and quantified. The spectrum 2303 accurately reproduces the sample composition. The peak 2303*a* corresponds to the residual water signal and the peaks 2303*b-c* correspond to the metabolites. 2301 and 2303 thus correspond to the conventional processing.

The spectrum 2304 is the spectrum obtained using a Fourier transform of the FID 2302. This spectrum is inoperative. It is very different from the spectrum 2303 and the metabolites cannot be identified or quantified. Taking account the module results in a false interpretation because of the acquisition with signal suppression of the reference species.

In practice, when the reference species is present in a much higher amount than that of the species to be characterized, the signal of the reference species will form a carrier for the signals of the other species.

In in vivo analyzes using water as the reference species, this will always be the case since water is present in an amount above $10^3$. Most often, it is present in an amount above $10^5$ or even $10^6$ times the amount of the other species. Thus, regardless of the relaxation time of the species, the water signal will form a carrier for the signals of the other species and taking into account the module will not remove the phase information of the signals of the species present in smaller quantity than water.

In other cases, where the reference species is initially present in a major amount but with a factor of 2, for example, and if the relaxation time of the reference species and of the species to be characterized are significantly different, then it may be advisable to modify the composition of the sample by performing at least one of the following steps:

adding solvent into the solution to increase the content thereof and thus to increase the signal of the reference species and let it act as the carrier;

adding a species producing no signal (no resonance frequency) but modifying the relaxation times to the sample. Such is the case of $CuSO_4$ for example.

Although the detailed description refers, by way of example, to the characterization of metabolites in a biological sample, the present invention also proves advantageous for analyzing a non-biological chemical composition. As a matter of fact, the invention makes it possible, for example, to identify chemical compounds in a solution comprising a reference species such as water or any other solvent and to measure the content of such compounds in this solution.

In addition, the invention applies whatever the nature of the reference species. Such reference species is often water as shown in the above examples but may be another species, for example a solvent other than water.

The invention is not limited to the embodiments described, but extends to all the embodiments covered by the claims.

The invention claimed is:

1. A method for the spectroscopic analysis, using nuclear magnetic resonance (NMR), of at least one sample comprising at least one species to be characterized and a reference species, the sample content of which is more than twice greater than the content of the at least one species to be characterized, with the method comprising the following steps:
   a. applying at least one constant field $B_0$ to the at least one sample,
   b. acquiring, by one or more antenna(s) one or more complex free induction decay (FID) signal(s) S(t), with each FID complex signal S(t) comprising a real part and an imaginary part; with the step of acquiring being performed so that, in each complex FID signal S(t) the amplitude of the signal of the reference species is at least twice greater than the amplitude of that of the least one species to be characterized;
   wherein the method also comprises at least the following step:
   c. for each complex FID signal S(t) calculating, using at least one processor, the module of each complex FID signal S(t).

2. The method according to claim 1, comprising, after the extraction of the module of each complex FID signal S(t), a step of identifying the nature and the content of the at least one species to be characterized from the module of each complex FID signal S(t).

3. The method according to claim 1, comprising, after the extraction of the module of each complex FID signal S(t), a step of applying a Fourier transform to a signal taking into account said FID module.

4. The method according to claim 1, wherein the content of the reference species in the solvent is at least greater than 5 times, preferably 10 times, preferably $10^3$ times to and more preferably $10^5$ times the content of each species to be characterized.

5. The method according to claim 1, wherein the signal of the reference species is used as a carrier for the signal of the at least one species to be characterized.

6. The method according to claim 1, wherein the content of the reference species in the sample is sufficiently higher than the content of the species to be characterized in the sample for the signal of the reference species to be used as a carrier for the signal of the at least one species to be characterized.

7. The method according to claim 1, wherein the relative contents of the reference species and of the at least one species to be characterized, as well as the relative relaxation times thereof are so selected that the amplitude of the signal of the reference species is at least twice greater than the amplitude of the signal of the at least one species of to be characterized.

8. The method according to claim 4, wherein the FID module of a sample comprising the species to be characterized is equal to IIS(t)II which is defined by the following equation:

$$IIS(t)II = |A_{H2O}(t) + A_0(t)\cos(\Delta\omega t + \Delta\varphi)|$$

wherein:
$\Delta\omega = \omega - \omega_{H2O}$ et $\Delta\varphi = \varphi - \varphi_{H2O}$ respectively correspond to the frequency and phase offsets between the at least one species to be characterized and the reference species,
$A_{H2O}(t)$ is the amplitude versus time of the FID signal of the reference species,
$A_0(t)$ is the amplitude versus time of the FID signal of the species to be characterized.

9. The method according to claim 1, wherein, during the step of acquiring, complex FID signals S(t) are acquired from multiple voxels of the sample, and wherein a step of spatial filtering is carried out after the calculation of the module of the complex FID signal S(t) for each one of the voxels.

10. The method according to claim 1, wherein, during the step of acquiring, a plurality of complex free induction decay (FID) signals is acquired, and wherein, after the step of generating a module for each complex FID signal S(t) of the plurality of complex FID signals S(t), a summation of the FID modules is performed to obtain a combined FID signal.

11. The method according to claim 10, wherein a Fourier transform is applied to said combined FID signal.

12. The method according to claim 1, wherein the antennas are coils and wherein the complex FID signals acquired are delivered by the same coil.

13. The method according to claim 1, wherein the antennas are coils and wherein the complex FID signals acquired are delivered by different coils.

14. The method according to claim 1, wherein the antennas are coils and wherein the acquired complex FID signals are delivered by different coils and several complex FID signals are acquired for at least some coils.

15. The method according to claim 13, wherein after the generation of a FID module for each complex FID signal, and prior to the summing of the FID modules to obtain a combined FID signal, a step of calculating a weighting factor for each coil is executed and each FID module is weighted by the weighting factor of the coil by which it has been delivered.

16. The method according to claim 1, wherein during the step of acquiring, a single complex FID signal S(t) is acquired and wherein a Fourier transform is applied to a FID module obtained by extracting the module from such single complex FID signal.

17. The method according claim 1, wherein, during the step of acquiring, a spatially encoded FID signal is acquired, the acquisition is repeated several times to obtain several encoded signals, with each of said encoded signals being subsequently decoded so that it is associated with a voxel of the sample and a FID module is generated for the FID signal associated with each voxel.

18. The method according to claim 1, wherein the sample comprises several species to be characterized.

19. The method according to claim 1, wherein the sample is a sample of a biological material, the reference species is water and the species to be characterized are metabolites.

20. The method according to claim 1, wherein the sample is a chemical composition, the reference species is a solvent and the species to be characterized are chemical compounds.

21. The method according to claim 1, wherein the constant field B0 is applied to several voxels of a sample and wherein the frequency spectra of the combined FID signals of the different voxels are used to generate one or more spectroscopic image(s).

22. The method according to claim 1, wherein the analysis is a spectroscopic or a spectrometric analysis.

23. The method according to claim 1, wherein the following steps are performed after the step of acquiring by one or more antenna(s) of one or more complex FID signal(s) S(t) before calculating the module:
  obtaining a FID spectrum S(ω) by applying a Fourier transform to the real and complex parts of the at least one complex FID signal S(t), with the FID spectrum S(ω) obtained then comprising the reference species and the species to be characterized and having two portions (UFR, DFR), each extending from the resonance frequency of the reference species ($F_{ORef}$) and respectively on either side of $F_{ORef}$, with the frequency of the species to be characterized being located on a first portion of the spectrum taken among said two portions (UFR, DFR);
  modeling the signal of the reference species Sref(t) from the real and complex parts of the at least one complex FID signal S(t);
  obtaining a spectrum Sref(ω) of the reference species by applying a Fourier transform to the modeling of the signal of the reference species Sref(t), with the spectrum Sref(ω) of the reference species then having two spectrum portions extending from the resonance frequency of the reference species ($F_{ORef}$) of the spectrum Sref(ω) and extending respectively on either side of $F_{ORef}$;
  obtaining a modified FID spectrum $\tilde{S}(\omega)$, by substituting a second portion of the FID spectrum S(ω), with said second portion being the portion taken from said two portions (UFR and DFR) of the spectrum S(ω) and which does not comprise the species to be characterized, by the portion of the spectrum Sref(ω) taken from the two portions of the spectrum extending from $F_{ORef}$ of the spectrum Sref(ω) and extending on the same side as said second portion of the spectrum S(ω);
  applying an inverse Fourier transform to the modified spectrum $\tilde{S}(\omega)$ to obtain a modified FID signal $\tilde{s}(t)$ in the time domain;
  calculating the module of the modified FID signal $\tilde{s}(t)$.

24. The method according to claim 23, comprising the following steps performed after the step of extracting the module of each complex FID signal S(t), after the step of calculating the module of the modified FID signal $\tilde{s}(t)$:
  subtracting the module of the complex FID signal S(t) signal from the module of the modified FID signal $\tilde{s}(t)$;
  subtracting the result obtained in the previous step from the module of the modified FID signal $\tilde{s}(t)$.

25. The method according to claim 23, comprising the following steps performed after the step of extracting the module of each complex FID signal S(t), after the step of calculating the module of the modified FID signal $\tilde{s}(t)$:
  applying a Fourier transform to the module of the complex FID signal S(t) and to the module of the modified FID signal $\tilde{s}(t)$ and then subtracting the spectrum of the module of the signal S(t) from the spectrum of the module of the modified FID signal $\tilde{s}(t)$;

subtracting the result obtained in the previous step from the spectrum of the module of the modified FID signal $\tilde{s}(t)$.

26. The method according to claim 23, wherein a step of identifying and/or quantifying the species to be characterized from the module of the modified FID signal $\tilde{s}(t)$ is executed during which a Fourier transform is applied to a signal comprising at least the module of the modified FID signal $\tilde{s}(t)$.

27. The method according to claim 23, wherein during the step of acquiring a plurality of complex FID signals S(t) is acquired, and wherein the step of calculating of the module of the modified signal $\tilde{s}(t)$ is performed for each modified FID signal $\tilde{s}(t)$.

28. The method according to claim 27, wherein after the step of calculating the module of the modified signal $\tilde{s}(t)$ for each complex FID signal S(t), a summation of the modules of the modified signals $\tilde{s}(t)$ is performed so as to obtain a combined FID signal and then a step of identifying and/or quantifying the species to be characterized is carried out which comprises applying a Fourier transform to said summation.

29. The method according to claim 23, wherein the antennas are coils and wherein the acquired complex FID signals S(t) are delivered by different coils and wherein, during the step of acquiring, complex FID signals S(t) from several voxels of the sample are acquired, and wherein, after completing the calculation of the module of the modified FID signal $\tilde{s}(t)$ for each voxel, a step of spatial filtering is executed.

30. A computer program product comprising instructions, which when executed by the at least one processor, executes at least the step of calculating the module of a FID signal of the method according to claim 1.

31. A system of spectroscopy using nuclear magnetic resonance (NMR) of at least one sample comprising at least one species to be characterized and a reference species taken from a solvent, with the content of the reference species in the sample being at least greater than twice the value of the at least one species to be characterized, with the system comprising at least one antenna so configured as to acquire one or more complex free induction decay (FID) signal(s) S(t) in the time domain, with each complex FID signal being generated by applying at least one field B0 to the at least one sample and comprising a real part and an imaginary part, characterized in that the system comprises processing means so configured as to calculate, for each complex FID signal, the module of each complex FID signal, and so configured as to perform, after the step of generating a FID module for each complex FID signal S(t) of the one or more complex FID signal(s) S(t), a summation of the FID modules to obtain a combined FID signal and preferably apply a Fourier transform to said combined FID signal.

32. The system according to claim 31, comprising one or more antenna(s) so configured as to acquire a plurality of complex FID signals S(t).

33. The system according to claim 31, wherein the antennas are coils and wherein the acquired complex FID signals S(t) are delivered by different coils, with the system processing means being so configured that:

during the step of acquiring complex signals FID S(t) delivered by multiple voxels of the sample are acquired, a step of spatial filtering is performed, after calculating the module of the modified FID signal $\tilde{s}(t)$ for each voxel.

34. The system according to claim 31, wherein the system comprises processing means so configured as to execute the steps of:

obtaining a FID spectrum S(ω) by applying a Fourier transform to the real and complex parts of the at least one complex FID signal S(t), with the FID spectrum S(ω) obtained then comprising the reference species and the species to be characterized and having two portions (UFR, DFR) each extending from the resonance frequency of the reference species ($F_{ORef}$) and respectively on either side of $F_{ORef}$, with the frequency of the species to be characterized being located on a first portion of the spectrum among said two portions (UFR, DFR); modeling the signal of the reference species Sref(t) from the real and complex parts of the at least one complex FID signal S(t);

obtaining a spectrum Sref(ω) of the reference species comprising only the reference species by applying a Fourier transform to the modeling of the signal of the reference species Sref(t), with the spectrum Sref(ω) of the reference species then having two portions extending from the resonance frequency of the reference species ($F_{ORef}$) of the spectrum Sref(ω) and extending respectively on either side of $F_{ORef}$;

obtaining a modified FID spectrum $\tilde{S}(ω)$, by substituting a second portion of the FID spectrum S(ω), with said second portion being the portion taken from said two portions (UFR and DFR) of the spectrum S(ω) and which does not comprise the species to be characterized, by the portion of the spectrum Sref(ω) taken from the two portions of the spectrum extending from $F_{ORef}$ of the spectrum Sref(ω) and which extends on the same side as said second portion of the spectrum S(ω);

applying an inverse Fourier transform to the modified spectrum $\tilde{S}(ω)$ to obtain a modified FID signal $\tilde{s}(t)$ in the time domain;

calculating the module of the modified FID signal $\tilde{s}(t)$.

35. The system according to claim 34, comprising processing means so configured as to execute the following steps, after the step of extracting the module of each complex FID signal S(t), after the step of calculating the module of the modified FID signal $\tilde{s}(t)$:

subtracting the module of the complex FID signal S(t) from the module of the modified FID signal $\tilde{s}(t)$; or applying a Fourier transform to the module of the complex FID signal S(t) and to the module of the modified FID signal $\tilde{s}(t)$ and then subtracting the spectrum of the module of the signal S(t) from the spectrum of the module of the modified FID signal $\tilde{s}(t)$;

subtracting the result obtained in the previous step from the module of the modified FID signal $\tilde{s}(t)$ respectively from the spectrum of the module of the modified FID signal $\tilde{s}(t)$.

* * * * *